US007871814B2

(12) United States Patent
Andino-Pavlovsky et al.

(10) Patent No.: US 7,871,814 B2
(45) Date of Patent: Jan. 18, 2011

(54) RECOMBINANT BICISTRONIC FLAVIVIRUSES AND METHODS OF USE THEREOF

(75) Inventors: Raul Andino-Pavlovsky, San Francisco, CA (US); Andres McAllister-Moreno, Geneva (CH)

(73) Assignee: The Regents of the University of California, Oakland, CA (US)

( * ) Notice: Subject to any disclaimer, the term of this patent is extended or adjusted under 35 U.S.C. 154(b) by 540 days.

(21) Appl. No.: 10/477,504

(22) PCT Filed: May 9, 2002

(86) PCT No.: PCT/US02/14783

§ 371 (c)(1),
(2), (4) Date: Jul. 14, 2004

(87) PCT Pub. No.: WO02/089840

PCT Pub. Date: Nov. 14, 2002

(65) Prior Publication Data

US 2004/0241821 A1 Dec. 2, 2004

(51) Int. Cl.
*C12N 15/36* (2006.01)
*A16K 35/00* (2006.01)

(52) U.S. Cl. ................................ 435/320.1; 424/218.1

(58) Field of Classification Search ............. 424/218.1, 424/19.1; 435/320, 69.1, 20.1, 320.1; 536/23.72
See application file for complete search history.

(56) References Cited

U.S. PATENT DOCUMENTS 6,392,028 B1 * 5/2002 Rice et al. ................ 536/23.72
6,893,866 B1 * 5/2005 Westaway et al. ........ 435/320.1

FOREIGN PATENT DOCUMENTS

WO WO 99/28487 A1 * 11/1998

OTHER PUBLICATIONS

Khromykh, A. et al. Subgenomic Replicons of the Flavivirus Kunjin: Construction and Applications (1997) Journal of Virology, 71(2): 1497-1505.*

Forns, X. et al. Hepatitis C virus lacking the hypervariable region 1 of the second envelope protein is infectious and causes acute reolving or persistent infection in chimpanzees (2002) Pro. Natl. Acad. Sci. 97(24):13318-13323.*

Monath, T.P. et al. Recombinant, chimaeric live, attenuated vaccine (ChimeriVaxTM) incorporating the envelope genes of Japanese encephalitis (Sa 14-14-2) virus . . . (1999) Vaccine 17:1869-1882.*

Lionnet et al. Protein Expression and Purification 2001, vol. 21, pp. 492-499.*

Fillippis et al. J. Medical Virol. 2002, vol. 68, pp. 620-627.*

Guirahoo et al. Virol. 1999, vol. 257, pp. 363-372.*

Chambers et al. J. Virol. 1999, vol. 73, No. 4, pp. 3095-3101.*

Lee et al. J. Virol. 2000, vol. 74, No. 1. pp. 24-32.*

The Lancet 2001, vol. 358, pp. 121-122.*

Ryman et al. Virol. 1998, vol. 244, pp. 59-65.*

Proutiski et al. Virus Research 1999, vol. 64, pp. 107-123.*

Worrow et al. The case law about *KSR International Co.* v. *Teleflex Inc.*—Conclude that Ordinary Innovation is Obviou, Published in 2007, in Website: www.fewick.com, pp. 1-2.*

Charles et al. Journal of Bacterialogy 1958, vol. 164, No. 1, pp. 123-129.*

Jin et al. Genetics 2005vol. 42, pp. 207-209.*

McAllister, A. et al., Recombinant yellow fever viruses are affective therapeutic vaccines for treatment of murine experimental solid tumors and pulmonary metastases, Oct. 2000. Journal of Virology, vol. 74, No. 19, pp. 9197-9205.

Qu, L., et al., Isolation and characterization of noncytopathic pestivirus mutants reveals role for nonstructural protein NS4B in viral cytopathogenicity, Nov. 2001, Journal of Virology, vol. 75, No. 22, 10651-10662.

Alexander, L. et al., Dicistronic Poliovirus as Expression Vectors for Foreign Genes, 1994, Aids Research and Human Retroviruses, vol. 10, Supplement 2, S57-S60.

* cited by examiner

*Primary Examiner*—Bao Li
(74) *Attorney, Agent, or Firm*—Paula A. Borden; Bozicevic, Field & Francis LLP

(57) ABSTRACT

The present invention provides recombinant bicistronic flaviviruses, particularly live attenuated recombinant bicistronic flavivirus, which comprise, in order from 5' to 3', a viral 5'UTR, an ORF encoding all viral proteins, an internal ribosome entry site, an exogenous nucleotide sequence that encodes an exogenous polypeptide, and a viral 3'UTR. Infection of a host cell with a recombinant flavivirus provides for expression of the exogenous nucleic acid in a host cell. Such recombinant flavivirus are useful for delivering a protein to a mammalian host; and for eliciting an immune response to the exogenous polypeptide.

24 Claims, 5 Drawing Sheets

FIG. 5A
FIG. 5B
FIG. 5C
FIG. 5D

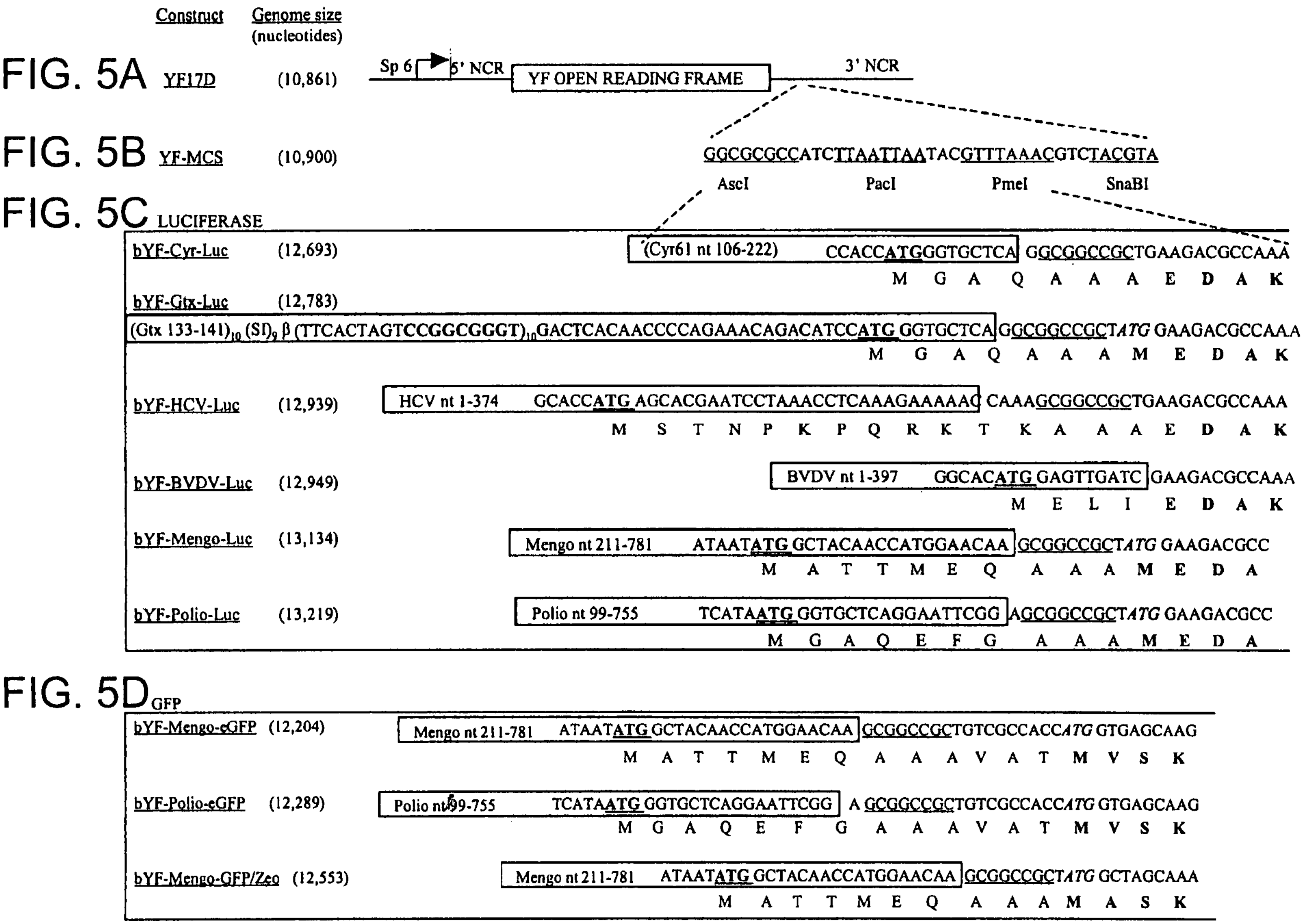

Construct
Genome size (nucleotides)
YF17D (10,861)
Sp 6
5' NCR
YF OPEN READING FRAME
3' NCR
YF-MCS (10,900)
GGCGCGCCATCTTAATTAAATACGTTTAAACGTCTACGTA
AscI PacI PmeI SnaBI
LUCIFERASE
bYF-Cyr-Luc (12,693)
(Cyr61 nt 106-222) CCACCATGGGTGCTCA GGCGGCGCTGAAGACGCCAAA
M G A Q A A A E D A K
bYF-Gtx-Luc (12,783)
(Gtx 133-141)10 (SI)9 β (TTCACTAGTCCGCGGT)10 GACTCACAACCCCAGAAACAGACATCCATG GGTGCTCA GGCGGCGCTATG GAAGACGCCAAA
M G A Q A A A M E D A K
bYF-HCV-Luc (12,939)
HCV nt 1-374 GCACCATG AGCACGAATCCTAAACCTCAAAGAAAAAC CAAAGCGGCGCTGAAGACGCCAAA
M S T N P K P Q R K T K A A A E D A K
bYF-BVDV-Luc (12,949)
BVDV nt 1-397 GGCACATG GAGTTGATC GAAGACGCCAAA
M E L I E D A K
bYF-Mengo-Luc (13,134)
Mengo nt 211-781 ATAATATG GCTACAACCATGGAACAA GCGGCCGCTATG GAAGACGCC
M A T T M E Q A A A M E D A
bYF-Polio-Luc (13,219)
Polio nt 99-755 TCATAATG GGTGCTCAGGAATTCGG AGCGGCCGCTATG GAAGACGCC
M G A Q E F G A A A M E D A
GFP
bYF-Mengo-eGFP (12,204)
Mengo nt 211-781 ATAATATG GCTACAACCATGGAACAA GCGGCCGCTGTCGCCACCATG GTGAGCAAG
M A T T M E Q A A A V A T M V S K
bYF-Polio-eGFP (12,289)
Polio nt 99-755 TCATAATG GGTGCTCAGGAATTCGG A GCGGCCGCTGTCGCCACCATG GTGAGCAAG
M G A Q E F G A A A V A T M V S K
bYF-Mengo-GFP/Zeo (12,553)
Mengo nt 211-781 ATAATATG GCTACAACCATGGAACAA GCGGCCGCTATG GCTAGCAAA
M A T T M E Q A A A M A S K

RECOMBINANT BICISTRONIC FLAVIVIRUSES AND METHODS OF USE THEREOF

STATEMENT REGARDING FEDERALLY SPONSORED RESEARCH

This invention was made with U.S. government support under grant nos. R21 AI 44343 and PO1 AI 46007 awarded by the National Institutes of Health. The government has certain rights in this invention.

CROSS-REFERENCE

This application is a national stage filing under 35 U.S.C. §371 of International Patent Application Ser. No. PCT/US02/14783, which was filed on May 9, 2002 and which was published in English under PCT Article 21(2) as WO 02/089840 on Nov. 14, 2002, which International Patent Application claims the benefit of priority of U.S. Provisional Patent Application No. 60/290,412, filed May 10, 2001, which applications are incorporated herein by reference in their entirety.

FIELD OF THE INVENTION

The invention relates generally to the field of recombinant viruses and induction of specific immunity.

BACKGROUND OF THE INVENTION

Yellow fever virus (YFV) 17D is a live, attenuated vaccine that has been used in humans for over 60 years. More than 300 million people have received the vaccine, with an outstanding record of safety and efficacy. After a single dose, neutralizing antibodies appear in nearly 100% of vaccines within 10 days. Immunity is extremely durable, and may be life long. YFV-17D is very immunogenic in humans, with a 90% immunizing dose of only 5-20 plaque-forming units of virus.

Yellow fever virus is the prototype member of a family of viruses, the flavivirus. Virions are spherical and about 40-50 nm in diameter. The nucleocapsid has icosahedral symmetry, contains the RNA genome, and a single core protein, and is surrounded by a lipid bilayer envelope. The viral genome is composed of a single-stranded RNA of positive polarity. The viral genome contains a single, long open reading frame that encodes 10 viral proteins.

Flaviviruses have been developed as vehicles for delivery of foreign proteins to a mammalian host for the purpose of generating an immune response to the foreign protein(s). Bonaldo et al. (2000) *Mem. Inst. Oswaldo Cruz* 95:215-223. In recombinant flaviviruses described to date, a nucleic acid molecule encoding the foreign protein is inserted into a region encoding viral proteins. Such recombinant viruses encode a polyprotein precursor in which the foreign protein is inserted, and which must then be cleaved out. A potential drawback to such recombinant viruses is that, because the polyprotein precursor includes an exogenous polypeptide, the viral proteins may be misfolded and therefore may not function normally.

There is a need in the art for improved recombinant viruses that are useful in delivering foreign proteins to a mammalian host. The present invention addresses this need.

Literature

WO 93/11250; Julius et al. (2000) *BioTechniques* 28:702-708; Pizzato et al. (1998) *Gene Therapy* 5:1003-1007; Lopez de Quinto et al. (1998) *Gene* 217:51-56; WO 00/65034; WO 00/16800; U.S. Pat. Nos. 5,854,037; 5,935,819; Bonaldo et al. (2000) *Mem. Inst. Oswaldo Cruz* 95:215-223.

SUMMARY OF THE INVENTION

The present invention provides live, replication-competent, recombinant bicistronic flaviviruses comprising, in order from 5' to 3', a 5' untranslated region (UTR) from the parent flavivirus, an open reading frame (ORF) encoding all viral proteins of the parent flavivirus, an internal ribosome entry site (IRES), an exogenous nucleic acid molecule, and a 3' UTR from the parent flavivirus. In general, the recombinant bicistronic flaviviruses of the invention are replication competent and are attenuated, e.g., they are live, attenuated viruses. In some embodiments, the flavivirus is a yellow fever virus. Accordingly, in some embodiments, the invention provides recombinant yellow fever viruses (YFV), particularly live attenuated recombinant YFV, which comprise an exogenous (i.e., non-YFV) nucleotide sequence which encodes an exogenous (i.e., non-YFV) polypeptide. Infection of a host cell with a recombinant bicistronic flavivirus provides for expression of the exogenous nucleic acid in a host cell and production of a polypeptide encoded by the exogenous nucleic acid. Such recombinant flavivirus are useful in eliciting an immune response to the exogenous polypeptide.

The recombinant live attenuated flavivirus express an exogenous nucleotide sequence which encodes an exogenous polypeptide, such as, but not limited to, a polypeptide obtained from a pathogenic agent other than the parent flavivirus used to generate the bicistronic flavivirus, a tumor antigen, or any other protein that has therapeutic activity. These recombinant flavivirus are useful, when introduced into a mammalian subject, in eliciting an immune response to the exogenous polypeptide in the subject. Thus, the recombinant flavivirus of the invention serve as immunization vehicles.

The invention provides methods of delivering a polypeptide to a host. The methods generally involve introducing a recombinant bicistronic flavivirus of the invention into a susceptible host. A wide variety of polypeptides can be expressed by the recombinant flavivirus of the invention, including those of microbial pathogens (e.g., bacteria, protozoa, viruses (other than the parent flavivirus used to generate the recombinant flavivirus of the invention), yeast, fungi, and the like); proteins having therapeutic activity; and tumor-associated antigens. In general, following infection of a host cell by the recombinant virus of the invention, the IRES site initiates translation of the exogenous polypeptide independently from translation of the viral polyprotein precursor. The exogenous polypeptide may then be exported to the host cell surface, may be presented on the cell surface as a peptide with a major histocompatibility antigen, may be secreted from the cell, or may remain in the cytoplasm of the cell.

The invention provides pharmaceutical compositions comprising recombinant flavivirus of the invention. Such compositions can be used, for example, to reduce the severity of disease, reduce the risk of clinical disease, prevent the onset of a disease and/or to ameliorate the disease via recruitment of the host immune system, and to deliver an exogenous polypeptide to a host.

The invention also provides methods of eliciting an immune response to an antigen in a mammalian subject. Such methods comprise administering a recombinant flavivirus of the invention to a mammalian subject so as to elicit an immune response to the exogerious polypeptide (i.e., the antigen). The antigen can be a host antigen or an antigen of a microorganism (e.g., bacteria, protozoa, viruses (other than the parent flavivirus used to generate the recombinant flavivirus of the invention), yeast, fungi, and the like).

The invention also provides methods of delivering a polypeptide having therapeutic activity to a host. Such methods generally involve administering a recombinant bicistronic flavivirus of the invention to a mammalian host. The exogenous polypeptide is then produced in a host cell. The therapeutic protein remains inside the cell, becomes associated with a cell membrane, or is secreted from the cell.

In the context of tumor immunotherapy, expression of an exogenous polypeptide in a host elicits an immune response to the tumor, with the result that the tumor cell mass and/or tumor cell number is reduced, development of a tumor is prevented or delayed, and/or the probability that a tumor will develop is reduced. Accordingly, the invention further provides methods of reducing or inhibiting tumor cell growth, and methods of reducing tumor cell mass and/or tumor cell numbers. Such methods comprise administering a recombinant flavivirus of the invention which comprises exogenous sequences encoding a tumor-associated antigen (TAA)/epitope to a host bearing a tumor, such that the recombinant flavivirus enters a cell of the host and the exogenous TAA polypeptide is expressed on the surface of a host cell, is presented in the context of an MHC molecule, or, alternatively, secreted from the host cell. An immune response is elicited to a tumor which bears on its surface an antigen which comprises the exogenous TAA polypeptide or which resembles the exogenous polypeptide sufficiently to elicit an immune response toward the tumor cell. The immune response to the tumor bearing the tumor-associated antigen on its surface is sufficient to reduce, inhibit, or eliminate the tumor.

The invention further provides methods of preventing tumor cell growth, and methods of reducing the probability that a tumor will form, comprising administering a recombinant flavivirus of the invention, which comprises a tumor-associated antigen/epitope-encoding nucleic acid, to a host not bearing a tumor, such that the recombinant flavivirus enters a host cell, the tumor-associated antigen is expressed on the host cell surface and/or presented in the context of an MHC molecule (e.g., MHC Class I), and an immune response is elicited to the tumor-associated antigen. The immune response to the tumor-associated antigen is sufficient to prevent, or reduce the likelihood, of tumor development in the host.

The invention further provides methods of producing an exogenous polypeptide. The methods generally involve introducing a recombinant bicistronic flavivirus of the invention into a susceptible host cell (e.g., by infection), under conditions that favor production of the exogenous polypeptide by the host cell. In some embodiments, the methods further comprise purifying the exogenous polypeptide.

A primary object of the invention is to provide a recombinant flavivirus that provides for production of an exogenous polypeptide in a mammalian host. An object of the invention is to provide for production of an exogenous polypeptide in a mammalian host that is suitable for induction of an immune response to the polypeptide in a host following infection with the recombinant flavivirus. Such exogenous polypeptides include, but are not limited to, an antigen produced by the host (e.g., a tumor antigen), or an antigen from a microorganism (e.g., bacteria, protozoa, viruses (other than the parent flavivirus used to generate the recombinant flavivirus of the invention), yeast, fungi, and the like). A further object of the invention is to provide for production of an exogenous polypeptide in a host, where the exogenous polypeptide provides a therapeutic activity.

An advantage of the invention is that the encoded exogenous polypeptide is expressed independently of the viral polyprotein precursor. Thus, the exogenous polypeptide undergoes intracellular co-translational and post-translational modifications in a manner that is substantially identical to the processing it undergoes in its native environment. Therefore, the exogenous polypeptide exhibits characteristics of the native protein, e.g., the protein as it is produced in its natural environment.

A further advantage of the invention is that, because the exogenous polypeptide is synthesized independently of the viral proteins, production of the exogenous polypeptide does not interfere with folding of the viral proteins, or with viral function.

An advantage of the invention is that the recombinant bicistronic flavivirus of the invention are live attenuated virus, which will continue to propagate until the intervention of the host's immune system.

Another advantage of the invention is that the recombinant bicistronic flavivirus exhibits low toxicity in vivo. Furthermore, the subject recombinant bicistronic flaviviruses are safe, i.e., they are non-pathogenic and thus do not produce a disease that wild-type flaviviruses might produce.

Yet another advantage of the invention is that the subject recombinant bicistronic flaviviruses can be used to deliver any protein (consistent with the upper size limits discussed herein) to a host.

Yet another advantage of the invention is that the subject recombinant bicistronic flaviviruses can be used to deliver a protein having therapeutic activity to a host.

Yet another advantage of the invention is that the recombinant flavivirus can express a polypeptide inside the host cell, and thus can provide for induction of an immune response, particularly a cellular immune response that involves, for example, antigen-specific cytotoxic T lymphocytes (CTLs).

Yet another advantage of the invention is that the immune response elicited using the recombinant flavivirus of the invention is not limited to the infected cells, as the immune system will also recognize cells bearing the antigen expressed by the recombinant flavivirus. For example, the production of a tumor antigen by the recombinant flavivirus can "break immune tolerance" to tumor antigens, and induce an immune response against the tumor effective to, for example, inhibit tumor growth.

These and other objects, advantages, and features of the invention will become apparent to those persons skilled in the art upon reading the details of the invention as more fully described below.

BRIEF DESCRIPTIONS OF THE DRAWINGS

Figure 1:
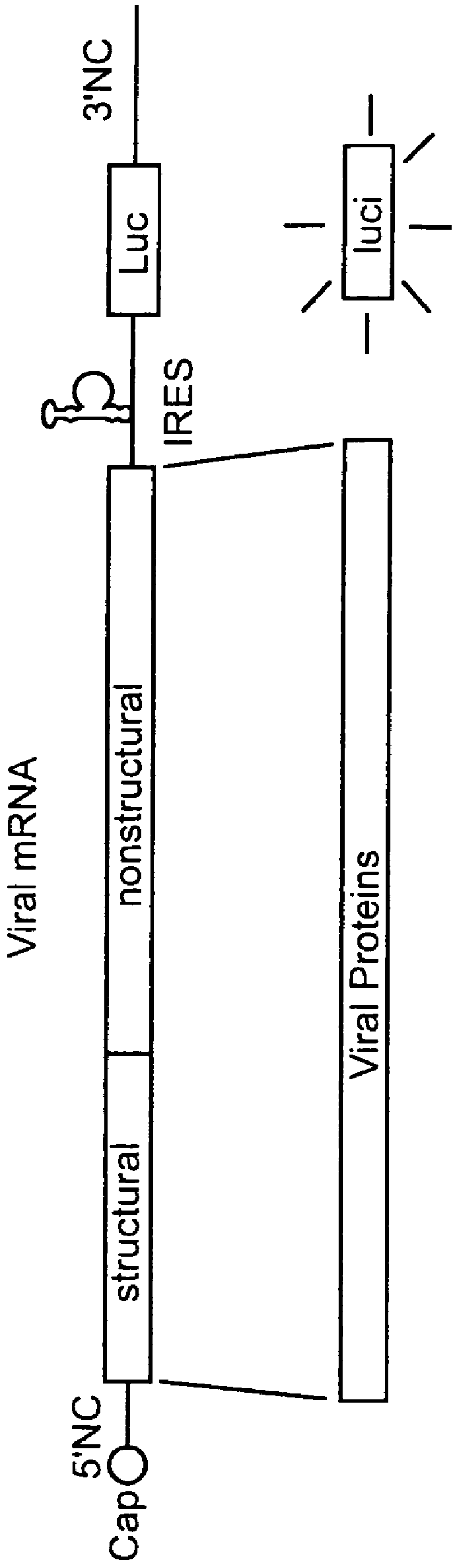
FIG. 1 is a schematic diagram of a recombinant bicistronic YFV vector for the expression of foreign proteins in accordance with the invention.

FIGS. 5A-D depict recombinant bicistronic YFV.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms “a”, “and”, and “the” include plural referents unless the context clearly dictates otherwise. Thus, for example, reference to “a recombinant flavivirus” includes a plurality of such flaviviruses and reference to “the exogenous polypeptide” includes reference to one or more exogenous polypeptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention.

Further, the dates of publication provided may be different from the actual publication dates which may need to be independently confirmed.

DEFINITIONS

The terms “polynucleotide” and “nucleic acid”, used interchangeably herein, refer to a polymeric forms of nucleotides of any length, either ribonucleotides or deoxynucleotides.

Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms “peptide,” “oligopeptide,” “polypeptide,” “polyprotein,” and “protein” are used interchangeably herein, and refer to a polymeric form of amino acids of any length, which can include coded and non-coded amino acids, chemically or biochemically modified or derivatized amino acids, and polypeptides having modified peptide backbones.

“Recombinant,” as used herein, means that a particular DNA sequence is the product of various combinations of cloning, restriction, and/or ligation steps resulting in a construct having a structural coding sequence distinguishable from homologous sequences found in natural systems. Generally, DNA sequences encoding the structural coding sequence can be assembled from cDNA fragments and short oligonucleotide linkers, or from a series of oligonucleotides, to provide a synthetic gene which is capable of being expressed in a recombinant transcriptional unit. Such sequences can be provided in the form of an open reading frame uninterrupted by internal nontranslated sequences, or introns, which are typically present in eukaryotic genes. Genomic DNA comprising the relevant sequences could also be used. Sequences of non-translated DNA may be present 5' or 3' from the open reading frame, where such sequences do not interfere with manipulation or expression of the coding regions. Thus, e.g., the term “recombinant” polynucleotide or nucleic acid refers to one which is not naturally occurring, or is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

By “construct” is meant a recombinant nucleic acid, generally recombinant DNA, which has been generated for the purpose of the expression of a specific nucleotide sequence(s), or is to be used in the construction of other recombinant nucleotide sequences.

Similarly, a “recombinant polypeptide” or “recombinant polyprotein” refers to a polypeptide or polyprotein which is not naturally occurring, or is made by the artificial combination of two otherwise separated segments of amino acid sequences. This artificial combination may be accomplished by standard techniques of recombinant DNA technology, such as described above, i.e., a recombinant polypeptide or recombinant polyprotein may be encoded by a recombinant polynucleotide. Thus, a recombinant polypeptide or recombinant polyprotein is an amino acid sequence encoded by all or a portion of a recombinant polynucleotide.

As used herein, the term “exogenous polypeptide” refers to a polypeptide that is not normally associated with a parent flavivirus in nature.

The term “bicistronic” refers to the existence in the recombinant flaviviruses of the invention of two unrelated cistrons which are expressed from a single viral transcriptional unit. The first cistron is an open reading frame encoding all viral proteins, while the second cistron initiates translation from an IRES element located between the two cistrons, and includes an open reading frame encoding an exogenous polypeptide.

The term “internal ribosomal entry site” or “IRES” refers to a viral, cellular, or synthetic (e.g., a recombinant) nucleotide sequence which allows for initiation of translation of an mRNA at a site internal to (e.g., at a site 3' of) a first coding region within the same mRNA or at a site 3' of the 5' end of the mRNA, to provide for translation of an operably linked coding region located downstream of (i.e., 3' of) the internal ribosomal entry site. This makes translation independent of the 5' cap structure, and independent of the 5' end of the mRNA. An IRES sequence provides necessary cis-acting sequences required for initiation of translation of an operably linked coding region.

The term “immunologically active” or “immunogenic” refers to the capability of the natural, recombinant, or synthetic peptide to induce a specific humoral and/or cellular immune response in a mammal. As used herein, “antigenic amino acid sequence,” “antigenic polypeptide,” or “antigenic peptide” means an amino acid sequence that, either alone or in association with an accessory molecule (e.g., a class I or class II major histocompatibility antigen molecule), can elicit an immune response in a mammal.

The terms “antigen” and “epitope” are well understood in the art and refer to the portion of a macromolecule which is specifically recognized by a component of the immune system, e.g., an antibody or a T-cell antigen receptor. Epitopes are recognized by antibodies in solution, e.g., free from other molecules. Epitopes are recognized by T-cell antigen receptor when the epitope is associated with a class I or class II major histocompatibility complex molecule. A “CTL epitope” is an epitope recognized by a cytotoxic T lymphocyte (usually a $CD8^+$ cell) when the epitope is presented on a cell surface in association with an MHC Class I molecule.

An “allergen” refers to a substance that can induce an allergic or asthmatic response in a susceptible subject.

As used herein the term “isolated” is meant to describe a compound of interest (e.g., a recombinant virus, a polypeptide, etc.) that is in an environment different from that in which the compound naturally occurs. “Isolated” is meant to include compounds that are within samples that are substantially enriched for the compound of interest and/or in which the compound of interest is partially or substantially purified.

By “subject” or “host” or “individual” or “patient,” which terms are used interchangeably herein, is meant any vertebrate subject, particularly a mammalian subject, e.g., a human. Other subjects may include ungulates (including sheep, pigs, cattle, and goats), equine hosts, rodents, lagomorphs, and so on. Of particular interest are those subjects susceptible to infection by a flavivirus, e.g., subjects who can support flavivirus replication.

A “biological sample” encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids and tissue samples.

The terms “treatment,” “treating,” and the like are used herein to generally refer to obtaining a desired pharmacologic or physiologic effect. The effect may be prophylactic in terms of completely or partially preventing a disease or symptom thereof and/or may be therapeutic in terms of a partial or complete cure for a disease and/or adverse effect attributable to the disease. “Treatment” as used herein covers any treatment of a disease in a mammal, e.g., a human, and includes: (a) preventing the disease from occurring in a subject which may be predisposed to the disease but has not yet been diagnosed as having it, e.g., reducing the risk that an individual will develop the disease, reducing the severity of a disease symptom; (b) inhibiting the disease, i.e., arresting its development; and (c) relieving the disease, i.e., causing regression of the disease.

Recombinant Bicistronic Flaviviruses

The present invention provides recombinant bicistronic flaviviruses, particularly live attenuated recombinant bicistronic flaviviruses, which comprise, in order from to 3', a 5'UTR from the parent flavivirus; an ORF encoding all proteins of the parent flavivirus; an internal ribosome entry site (IRES), an exogenous nucleic acid molecule (i.e., a nucleic acid molecule from other than the parent flavivirus) which comprises a nucleotide sequence that encodes an exogenous polypeptide (i.e., a polypeptide from other than the parent flavivirus); and a 3' UTR from the parent flavivirus. Such recombinant flavivirus are useful for delivering the encoded exogenous polypeptide to a mammalian host. Such recombinant flavivirus are also useful in eliciting an immune response to the exogenous polypeptide. For simplicity, “exogenous” is used throughout as exemplary of such sequences, but is not intended to be limiting.

The subject invention provides compositions and methods for generating and using recombinant flaviviruses to express exogenous nucleic acid molecules and to produce exogenous polypeptides encoded by the exogenous nucleic acid molecules. FIG. 1 is a schematic diagram of a recombinant bicistronic YFV vector for the production of foreign proteins. In FIG. 1, the bar represents recombinant YFV genomic RNA; the structural and non-structural viral genes are indicated within corresponding boxes, the exogenous nucleic acid molecule (e.g. Luc=luciferase) at the 3' end of the viral genome is indicated by a striped box. The sequences immediately 5' of the luciferase-encoding region correspond to an IRES element that allows for the expression of the luciferase coding region.

Yellow fever virus (YFV) is one non-limiting example of a flavivirus. The following description of YFV is generally applicable to other flaviviruses. Yellow fever virus is an enveloped, positive-stranded RNA virus and a member of the flaviviridae genus. The viral genome is approximately 11 kb in length and encodes a single polypeptide precursor that encodes 10 viral proteins.

Bicistronic recombinant flaviviruses of the invention comprise an IRES element and a nucleic acid encoding an exogenous polypeptide inserted at the 3' end of the ORF encoding all proteins of the parent flavivirus. The IRES element is inserted after the ORF encoding all proteins of the parent flavivirus. The IRES element initiates the expression of the encoded exogenous polypeptide independently of the viral proteins which are translated by the normal flavivirus cap-dependent initiation.

The starting flavivirus, which is subsequently modified to include the exogenous sequences, is also referred to herein as the “parent” flavivirus. The parent flavivirus can be a native flavivirus (either pathogenic or, preferably, non-pathogenic), an attenuated flavivirus, a vaccine flavivirus strain, or a recombinant flavivirus. In many embodiments, the parent flavivirus is a live, attenuated flavivirus. Any of a variety of strains of flavivirus can be used in generating recombinant flavivirus as described herein.

Flavivirus which are suitable for use in generating recombinant flavivirus of the invention include, but are not limited to, yellow fever virus (YFV); Dengue virus, including Dengue types 1-4; Japanese Encephalitis virus; Murray Valley Encephalitis virus; St. Louis Encephalitis virus; West Nile virus; tick-borne encephalitis virus; Hepatitis C virus; Kunjin virus; Central European encephalitis virus; Russian spring-summer encephalitis virus; Powassan virus; Kyasanur Forest disease virus; and Omsk hemorrhagic fever virus. In many embodiments, the flavirus used as the starting flavivirus to generate recombinant flavivirus is YFV.

The nucleotide sequences of a number of YFV strains are available in public databases, including, e.g., GenBank. An exemplary strain is "YFV 17D." The nucleotide sequence of the YFV genome, as well as the amino acid sequence of the encoded viral polyprotein are found under GenBank Accession No. X03700, and are also described in Rice et al. ((1985) *Science* 229:726-733), both of which are incorporated herein by reference in their entirety for the nucleotide and protein sequences disclosed therein. Production of yellow fever virions (viral particles) is well known in the art.

In many embodiments, the flavivirus nucleotide sequences of the recombinant flavivirus are wild-type, i.e., they are sequences found in nature. In other embodiments, the flavivirus nucleotide sequences contain one or more mutations compared to a wild-type flavivirus. In still other embodiments, the flavivirus portion of the recombinant flavivirus is derived from two or more different flaviviruses, i.e., the flavivirus used to construct a recombinant flavivirus is a chimeric flavivirus.

In general, an exogenous nucleic acid molecule(s) in the recombinant flaviviruses comprises a nucleotide sequence encoding an exogenous polypeptide. The exogenous nucleic acid sequence are positioned 3' to a viral and/or cellular IRES element for independent expression of the encoded exogenous polypeptide, while viral proteins are translated from the cap structure at the 5' end of the genome. The insertion of the IRES element and the exogenous nucleic acid outside of the flavivirus ORF, insures that there is no disruption of flavivirus protein function, and/or proteolytic processing of the viral polypeptide, and/or viral replication. Whether viral replication is adversely affected can be determined using well-established techniques, including, but not limited to, a plaque assay, and a one-step growth curve assay.

Unlike other vectors which will produce only one cycle of antigen expression and/or which will stop expression without the intervention of the host immune system, the replication-competent recombinant virus of the invention will continue to propagate until the immune system is sufficiently activated to halt the infection. This produces a stronger immune response against the exogenous antigenic peptide produced from the flavivirus as compared to the immune response that would be elicited using conventional expression vectors (e.g., a viral replicon).

The recombinant flavivirus also exhibits low toxicity to a host upon infection. For example, YF-17D is a very safe and effective live viral vaccine, prepared from infected chicken embryos under standards developed by the World Health Organization. After vaccination, immunity is elicited within 10 days in over 95% of vaccines and neutralizing antibodies directed against the virus can be detected for more than 35 years. The vaccine safety record is outstanding: serious adverse reactions to YF-17D vaccine are extremely uncommon, and reversion to wild type is virtually non-existent.

Any of a variety of naturally-occurring and synthetic (e.g. recombinant) IRES sequences can be used in the recombinant bicistronic flaviviruses of the invention. Naturally occurring IRES sequences are known in the art and include, but are not limited to, IRES sequences derived from mengovirus, bovine viral diarrhea virus (BVDV), hepatitis C virus (HCV; e.g., nucleotides 1202-1812 of the nucleotide sequence provided under GenBank Accession number AJ242654), GTX, Cyr61a, Cyr61b, poliovirus, the immunoglobulin heavy-chain-binding protein (BiP), immunoglobulin heavy chain, a picomavirus, murine encephalomyocarditis virus, poliovirus, and foot and mouth disease virus (e.g., nucleotide numbers 600-1058 of the nucleotide sequence provided under GenBank Accession No. AF308157). Other IRES sequences such as those reported in WO 96/01324; WO 98/49334; WO 00/44896; and U.S. Pat. No. 6,171,821 can be used in the recombinant flaviviruses of the invention.

Mutants, variants and derivatives of naturally occurring IRES sequences may be employed in the present invention provided they retain the ability to initiate translation of an operably linked coding sequence located 3' of the IRES. An IRES sequence suitable for use in the present invention has at least about 50%, at least about 60%, at least about 70%, at least about 80%, at least about 90%, at least about 95%, or more, nucleotide sequence identity with a naturally occurring IRES. An IRES sequence suitable for use in the present invention may also be a fragment of a naturally occurring IRES, provided the fragment functions to allow ribosome attachment and initiate translation of an operably linked 3' coding region.

Additional features can be incorporated into the design of a replication-competent recombinant flavivirus virus of the invention, such as polylinker sequences (e.g., EcoR1, NotI, BssH2, and XhoI) to facilitate the ease of insertion of desired foreign sequences into the recombinant vector.

More than one nucleic acid sequence encoding an exogenous protein or polypeptide to be produced can be included in the recombinant replication-competent flavivirus virus which, as a result, produces the corresponding number of exogenous proteins or polypeptides. The two or more nucleic acid sequences can each encode a different product or can encode the same product (e.g., if enhanced production of a protein or polypeptide is desired).

The addition of an IRES element and an exogenous nucleic acid 3' of the viral genome can be accomplished by standard techniques of molecular biology, such as described in numerous standard protocol texts, including e.g., *Current Protocols in Molecular Biology*, (F. M. Ausubel, et al., Eds. 1987, and updates. Example 1 provides further guidance for how particular recombinant flaviviruses were generated. Using these guidelines, any of a variety of IRES elements and exogenous nucleic acids can be added to the flavivirus genome.

The exogenous nucleic acid molecule is from about 12 to about 18, from about 15 to about 24, from about 21 to about 30, from about 30 to about 60, from about 60 to about 90, from about 90 to about 120, from about 120 to about 150, from about 150 to about 180, from about 180 to about 240, from about 240 to about 300, from about 300 to about 600, from about 600 to about 1200, from about 1200 to about 1500, from about 1500 to about 2100, from about 2100 to about 2400, or from about 2400 to about 3000 nucleotides in length.

The encoded exogenous polypeptide is from about 4 to about 6, from about 5 to about 8, from about 7 to about 10, from about 10 to about 20, from about 20 to about 30, from about 30 to about 40, from about 40 to about 50, from about 50 to about 60, from about 60 to about 80, from about 80 to about 100, from about 100 to about 200, from about 200 to about 400, from about 400 to about 500, from about 500 to about 700, from about 700 to about 800, or from about 800 to about 1000 amino acids in length.

Recombinant bicistronic flaviviruses of the invention enter a host cell, and subsequently the host cell produces the exogenous polypeptide encoded by the recombinant flavivirus. In some embodiments, the exogenous polypeptide remains intracellular. In other embodiments, the exogenous polypeptide is associated with the cell surface. In still other embodiments, the exogenous polypeptide is secreted from the cell.

Recombinant bicistronic flaviruses of the invention are useful for delivering a polypeptide to a host. A subject recombinant bicistronic flavivirus is administered to a mammalian host. Subsequently, the subject recombinant bicistronic flavivirus enters a host cell, and the exogenous polypeptide is produced by the cell. The exogenous polypeptide remains intracellular, becomes associated with a cell membrane (e.g., the plasma membrane), or is secreted from the cell.

Exogenous polypeptides can be a polypeptide from any of a variety of pathogenic organisms, including, but not limited to, viruses, bacteria, yeast, fungi, and protozoa; a tumor-associated antigen; a "self" antigens; a foreign antigen from other than a pathogenic microorganism; a protein that has a therapeutic activity; and the like.

Where the polypeptide comprises one or more antigenic epitopes, any nucleic acid molecule comprising a nucleotide sequence which encodes a polypeptide which, when produced by a cell infected by a recombinant flavivirus of the invention, increases an immune response is suitable for use in the present invention. Nucleic acid sequences encoding one or more exogenous polypeptides (e.g., antigens or epitopes) of interest can be included in a recombinant bicistronic flavivirus of the invention. If more than one exogenous antigen or epitope of interest is encoded by the exogenous nucleic acid sequences, they can be antigens or epitopes of a single pathogen or antigens or epitopes from more than one (different) pathogen. In many embodiments, such an organism is a pathogenic microorganism. For example, such an exogenous epitope may be found on bacteria, parasites, viruses, yeast, or fungi that are the causative agents of diseases or disorders. In other embodiments, the antigen is an allergen. In still other embodiments, the antigen is a tumor-associated antigen. In still other embodiments, the antigen is a sperm-associated antigen. In further embodiments, the antigen is one that produces adverse physiological effects in a vertebrate host, including, but not limited to, a venom.

Pathogenic viruses include, but are not limited to, Retroviridae (e.g., human immunodeficiency viruses, such as HIV-1 (also referred to as HTLV-III, LAV or HTLV-III/LAV, or HIV-III); and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Bimaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses); Poxyiridae (variola viruses, vaccinia viruses, pox viruses); and Iridoviridae (e.g., African swine fever virus); Hepatitis C virus; and unclassified viruses (e.g., the agent of delta hepatitis (thought to be a defective satellite of hepatitis B virus); Norwalk and related viruses, and astroviruses).

Pathogenic bacteria include, but are not limited to, *Helicobacterpyloris, Borelia burgdorferi, Legionella pneumophila, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyrogenes* (Group A *Streptococcus*), *Streptococcus agalactiae* (Group B *Streptococcus*), *Streptococcus* (viridans group), *Streptococcus faecalis, Streptococcus bovis, Streptococcus* (*anaerobic* sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum*, pathogenic strains of *Escherichia coli, Streptobacillus moniliformis, Treponema pallidium, Treponema pertenue, Leptospira*, and *Actinomyces israelli.*

Infectious fungi include, but are not limited to, *Cryptococcus neoformans, Histoplasma capsulatum, Coccidioides immitis, Blastomyces dermatitidis, Chlamydia trachomatis, Candida albicans.*

Infectious protozoa include, but are not limited to, *Plasmodium* spp., e.g., *Plasmodium falciparum*; Trypanosomes, e.g., *Trypanosoma cruzi*; and *Toxoplasma gondii.*

Allergens include, but are not limited to, pollens, insect venoms, animal dander dust, fungal spores and drugs (e.g. penicillin). Examples of natural, animal and plant allergens include proteins specific to the following genera: Canine (*Canis familiaris*); *Dermatophagoides* (e.g. *Dermatophagoides farinae*); *Felis* (*Felis domesticus*); *Ambrosia* (*Ambrosia artemiisfolia; Lolium* (e.g. *Lolium perenne* or *Lolium multiflorum*); *Cryptomeria* (*Cryptomeria japonica*); *Alternaria* (*Alternaria alternata*); *Alder; Alnus* (*Alnus gultinosa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Charnaecyparis obtusa*); *Periplaneta* (e.g. *Periplaneta americana*); *Agropyron*(e.g. *Agropyron* repens); *Secale* (e.g. *Secale cereale*); *Triticum* (e.g. *Triticum aestivum*); *Dactylis* (e.g. *Dactylis glomerata*); *Festuca*(e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis*(e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*).

Any of a variety of known tumor-associated antigens (TAA) can be inserted into flavivirus of the invention. The entire TAA may be, but need not be, inserted. Instead, a portion of a TAA, e.g., an epitope, particularly an epitope that is recognized by a CTL, may be inserted. Tumor-associated antigens (or epitope-containing fragments thereof) which may be inserted into flavivirus include, but are not limited to, MAGE-2, MAGE-3, MUC-1, MUC-2, HER-2, high molecular weight melanoma-associated antigen MAA, GD2, carcinoembryonic antigen (CEA), TAG-72, ovarian-associated antigens OV-TL3 and MOV 18, TUAN, alpha-feto protein (AFP), OFP, CA-125, CA-50, CA-19-9, renal tumor-associated antigen G250, EGP-40 (also known as EpCAM), S100 (malignant melanoma-associated antigen), p53, prostate tumor-associated antigens (e.g., PSA and PSMA), and p21ras.

Other antigens of interest include, but are not limited to, sperm-associated antigens, venoms, hormones, and the like. Sperm-associated proteins are known in the art, and a nucleic acid molecule encoding any such protein is suitable for use herein. See, e.g., Primakoff (1994) *Reproductive Immunol.*

31:208-210; Naz et al. (1995) *Human Reprod. Update* 1:1-18; Kerretal. (1998) *J. Reprod. Immunol.* 40:103-118; and U.S. Pat. No. 6,197,940. Hormones of interest include, but are not limited to, human chorionic gonadotrophin (hCG). Hormones such as hCG are useful to elicit specific antibodies, for use as contraceptive. Venoms of interest include those from any poisonous animal, e.g., snake venoms, including, but not limited to, α-neurotoxins, kappa toxins, β-neurotoxins, dendrotoxins, cardiotoxins, myotoxins, and hemorrhaging. Of particular interest in many embodiments are modified venoms that elicit specific antibodies, but are not themselves toxic. Such modified venoms are useful to elicit an immune response to a venom, and in many embodiments, elicit a protective immune response such that, upon subsequent exposure to the venom from an animal source, any adverse physiological effects of the venom are mitigated.

A "therapeutic protein" includes a protein that the host does not produce but is in need of; a protein that the host does not normally produce, but which has a therapeutic activity; a protein that the host produces, but produces in inadequate amounts; a protein that the host produces but in a form which is inactive, or which has reduced activity compared with an activity normally associated with the protein; or a protein that the host produces in adequate amounts and with normal activity associated with that protein. Therapeutic proteins include naturally-occurring proteins, and recombinant proteins whose amino acid sequences differ from a naturally-occurring counterpart protein, which recombinant proteins have substantially the same, an altered activity, or enhanced activity relative to a naturally-occurring protein. Proteins that have therapeutic activity include, but are not limited to, cytokines, including, but not limited to, interleukins, endothelin, colony stimulating factors, tumor necrosis factor, and interferons; hormones, including, but not limited to, a growth hormone, insulin; growth factors, including, but not limited to human growth factor, insulin-like growth factor; bioactive peptides; trophins; neurotrophins; soluble forms of a membrane protein including, but not limited to, soluble CD4; enzymes; regulatory proteins; structural proteins; clotting factors, including, but not limited to, factor XIII; chemokines; erythropoietin; tissue plasminogen activator; etc.

The nucleic acid molecule encoding the exogenous protein to be produced by a host cell following infection of the host cell by the recombinant flavivirus to the present invention can be obtained by techniques known in the art, including but not limited to, chemical or enzymatic synthesis, purification from genomic DNA of the microorganism, by purification or isolation from a cDNA encoding the exogenous protein, by cDNA synthesis from RNA of an organism, or by standard recombinant methods (Maniatis et al., Molecular Cloning, A Laboratory Manual, 1982, Cold Spring Harbor Laboratory, Cold Spring Harbor, N.Y.). Nucleotide sequences encoding many of the above-listed exogenous proteins are publicly available. Variant of such sequences can readily be generated by those skilled in the art using standard recombinant methods, including site-directed and random mutagenesis. The nucleic acid molecule encoding the exogenous polypeptide can further include sequences that direct secretion of the protein from the cell, sequences that alter RNA and/or protein stability, and the like.

Compositions Comprising Recombinant Bicistronic Flaviviruses of the Invention The present invention further provides compositions, including pharmaceutical compositions, comprising a recombinant flavivirus of the invention.

Compositions comprising a recombinant flavivirus of the invention may include a buffer, which is selected according to the desired use of the recombinant flavivirus, and may also include other substances appropriate to the intended use. Where the intended use is to elicit or increase an immune response, the composition is referred to as "an immunogenic composition." Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, A. Gennaro (2000) "Remington: *The Science and Practice of Pharmacy",* 20th edition, Lippincott, Williams, & Wilkins; *Pharmaceutical Dosage Forms and Drug Delivery Systems* (1999) H. C. Ansel et al., eds $7^{th}$ ed., Lippincott, Williams, & Wilkins; and *Handbook of Pharmaceutical Excipients* (2000) A. H. Kibbe et al., eds., $3^{rd}$ ed. Amer. Pharmaceutical Assoc.

Pharmaceutical Formulations, Routes of Administration, and Dosages

Formulations

The invention further provides pharmaceutical formulations comprising a recombinant bicistronic flavivirus of the invention. Pharmaceutical formulations can comprise more than one different recombinant flavivirus, e.g., recombinant flaviviruses comprising different exogenous nucleic acid molecules.

Pharmaceutical compositions can be prepared in various forms, such as granules, tablets, pills, suppositories, capsules, injectable formulations, suspensions, sprays, suppositories, transdermal applications (e.g., patches, etc.), salves, lotions and the like. Pharmaceutical grade organic or inorganic carriers and/or diluents suitable for oral and topical use can be used to make up compositions containing the therapeutically active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

For or oral preparations, the formulations can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

When used as an immunogenic composition (e.g., a "vaccine"), a recombinant flavivirus of the invention can be formulated in a variety of ways. In general, the immunogenic composition of the invention is formulated according to methods well known in the art of vaccine preparation, using suitable pharmaceutical carrier(s) and/or vehicle(s). A suitable vehicle is sterile saline. Other aqueous and non-aqueous isotonic sterile injection solutions and aqueous and non-aqueous sterile suspensions known to be pharmaceutically acceptable carriers and well known to those of skill in the art may be employed for this purpose.

Optionally, a vaccine composition ("immunogenic composition") of the invention may be formulated to contain other components, including, e.g., adjuvants, stabilizers, pH adjusters, preservatives and the like. Such components are well known to those of skill in the vaccine art. Adjuvants include, but are not limited to, aluminum salt adjuvants (Nicklas (1992) *Res. Immunol.* 143:489-493); saponin adjuvants; Ribi's adjuvants (Ribi ImmunoChem Research Inc., Hamilton, Mont.); Montanide ISA adjuvants (Seppic, Paris, France); Hunter's TiterMax adjuvants (CytRx Corp., Norcross, Ga.); Gerbu adjuvants (Gerbu Biotechnik GmbH, Gaiberg, Germany); and nitrocellulose (Nilsson and Larsson (1992) *Res. Immunol.* 143:553-557). In addition, other components that may modulate an immune response may be included in the formulation, including, but not limited to, cytokines, such as interleukins; colony-stimulating factors (e.g., GM-CSF, CSF, and the like); and tumor necrosis factor.

Routes of Administration

Conventional and pharmaceutically acceptable routes of administration include intranasal, intramuscular, intratracheal, intratumoral, subcutaneous, intradermal, vaginal, intrapulmonary, intravenous, rectal, nasal, oral and other parenteral routes of administration. Routes of administration may be combined, if desired, or adjusted depending upon the antigenic peptide or the disease. The composition can be administered in a single dose or in multiple doses, and may encompass administration of booster doses, to elicit and/or maintain immunity.

When they are used as vaccines, the recombinant flavivirus of the present invention are administered to an individual using known methods. They will generally be administered by the same routes by which conventional (presently-available) vaccines are administered and/or by routes that mimic the route by which infection by the pathogen of interest occurs.

Dosages

The recombinant flavivirus vaccine is administered in an "effective amount" that is, an amount effective to achieve production of the exogenous polypeptide in the host at a desired level. In general, it is expected that each dose of recombinant bicistronic flavivirus will be sufficient to generate, upon infection of host cells, about 1-1000 μg of protein, generally from about 1-200 μg, normally from about 10-100 μg. The dose of recombinant bicistronic flavivirus administered to an individual will generally be in a range of from about $10^2$ to about $10^7$, from about $10^3$ to about $10^6$, or from about $10^4$ to about $10^5$ plaque forming units (PFU).

In some embodiments, an "effective amount" of a subject recombinant bicistronic flavivirus is an amount sufficient to achieve a desired therapeutic effect.

In some embodiments, an "effective amount" of a subject recombinant bicistronic flavivirus is an amount of recombinant flavivirus that is effective in a selected route of administration to elicit an immune response to the exogenous antigen.

In many embodiments, e.g., where the exogenous polypeptide is one associated with a pathogenic microorganism, an "effective amount" is an amount that is effective to facilitate protection of the host against infection, or symptoms associated with infection, by a pathogenic organism, e.g., to reduce a symptom associated with infection, and/or to reduce the number of infectious agents in the individual. In these embodiments, an effective amount reduces a symptom associated with infection and/or reduces the number of infectious agents in an individual by at least about 10%, at least about 20%, at least about 30%, at least about 40%, at least about 50%, at least about 60%, at least about 70%, at least about 80%, or at least about 90%, or more, when compared to the symptom or number of infectious agents in an individual not treated with the recombinant bicistronic flavivirus, or treated with the parent flavivirus. Symptoms of infection by a pathogenic microorganism, as well as methods for measuring such symptoms, are known in the art. Methods for measuring the number of pathogenic microorganisms in an individual are standard in the art.

In some embodiments, e.g., where the exogenous polypeptide is a tumor-associated antigen, an "effective amount" of a recombinant flavivirus vaccine is an amount of recombinant flavivirus that is effective in a route of administration to elicit an immune response effective to reduce or inhibit tumor cell growth, to reduce tumor cell mass or tumor cell numbers, or to reduce the likelihood that a tumor will form. In these embodiments, an effective amount reduces tumor growth and/or the number of tumor cells in an individual by at least about 10%, at least about 20%, at least about 30%, at least about 40%, at least about 50%, at least about 60%, at least about 70%, at least about 80%, or at least about 90%, or more, when compared to the tumor growth and/or number of tumor cells in an individual not treated with the recombinant bicistronic flavivirus, or treated with the parent flavivirus. Methods of measuring tumor growth and numbers of tumor cells are known in the art.

In other embodiments, e.g., where the exogenous polypeptide is a sperm-associated antigen, or a hormone such as hCG, an "effective amount" of a recombinant bicistronic flavivirus is an amount effective to reduce fertility in the individual. In these embodiments, an effective amount reduces fertility in an individual by at least about 10%, at least about 20%, at least about 30%, at least about 40%, at least about 50%, at least about 60%, at least about 70%, at least about 80%, or at least about 90%, or more, when compared to fertility in an individual not treated with the recombinant bicistronic flavivirus, or treated with the parent flavivirus.

In still other embodiments, e.g., where the exogenous polypeptide is a venom or a modified venom, an "effective amount" of a recombinant bicistronic flavivirus is an amount effective to reduce the magnitude of an adverse physiological effect of subsequent exposure to the venom from an animal source. In these embodiments, an effective amount reduces an adverse physiological effect associated with exposure to an animal venom in an individual by at least about 10%, at least about 20%, at least about 30%, at least about 40%, at least about 50%, at least about 60%, at least about 70%, at least about 80%, or at least about 90%, or more, when compared to the physiological effect of the animal venom in an individual not treated with the recombinant bicistronic flavivirus, or treated with the parent flavivirus.

The amount of recombinant flavivirus in each dose is selected as an amount which induces an immune response to the encoded exogenous antigen, and/or which induces an immunoprotective or other immunotherapeutic response without significant, adverse side effects generally associated with typical vaccines. Such amount will vary depending upon which specific exogenous polypeptide is employed, whether or not the vaccine formulation comprises an adjuvant, and a variety of host-dependent factors.

An effective dose of recombinant flavivirus nucleic acid-based vaccine will generally involve administration of from about 1-1000 μg of nucleic acid. Alternatively, an effective dose of recombinant flavivirus vaccine will generally be in a range of from about $10^2$ to about $10^7$, from about $10^3$ to about $10^6$, or from about $10^4$ to about $10^5$ plaque forming units (PFU). An optimal amount for a particular vaccine can be ascertained by standard studies involving observation of antibody titers and other responses in subjects. The levels of immunity provided by the vaccine can be monitored to determine the need, if any, for boosters. Following an assessment of antibody titers in the serum, optional booster immunizations may be desired. The immune response to the protein of this invention is enhanced by the use of adjuvant and/or an immunostimulant.

Uses of Recombinant Flaviviruses of the Invention

Recombinant flaviviruses of the invention are useful to deliver a polypeptide to a mammalian host; and to elicit or increase an immune response to an antigen encoded by the recombinant flavivirus. Recombinant flavivirus of the present are also useful for producing the exogenous polypeptide in host cells, such as mammalian, particularly human, cells or other cell types. The exogenous protein can further be isolated or purified using standard methods.

Methods of Using the Recombinant Flaviviruses of the Invention

The present invention provides methods for delivering a therapeutic polypeptide to a mammalian host; methods for eliciting an immune response to an antigen in a vertebrate host; and methods for producing an exogenous polypeptide in a vertebrate host cell.

Methods for Delivering a Therapeutic Polypeptide to a Mammalian Host

The present invention provides methods for delivering a polypeptide to a mammalian host. The methods generally involve administering a recombinant bicistronic flavivirus of the invention to a vertebrate host, wherein the flavivirus enters a host cell, the exogenous polypeptide is expressed independently of the viral proteins. In some embodiments, the exogenous polypeptide remains intracellular. In other embodiments, the exogenous polypeptide becomes associated with the plasma membrane of a host cell. In other embodiments, the exogenous polypeptide is secreted from the cell. In those embodiments in which the exogenous polypeptide is secreted from the cell, the exogenous polypeptide can be secreted into the extracellular milieu, e.g., the interstitial fluid; and/or the exogenous polypeptide can enter the blood stream; and/or the exogenous polypeptide can bind to and/or enter a cell other than the cell in which it was produced.

In many embodiments, the exogenous polypeptide is one that has therapeutic activity, such that when the protein is produced in the mammalian host, a therapeutic effect is achieved. Whether, and at what level, a therapeutic protein is produced in an individual is readily determined using any known method, e.g., methods for detecting the presence of and/or measuring the amount of a protein, including, but not limited to, an enzyme-linked immunosorbent assay, a radioimmunoassay, and the like, using specific antibody; and methods for detecting the presence of and/or measuring the amount of a biological activity associated with the protein. Whether a therapeutic effect is achieved can be determined using a method appropriate to the particular therapeutic effect. For example, whether a therapeutic effect is achieved when insulin is delivered to a host using the subject method can be determined by measuring glucose levels in the individual.

Methods of delivering a therapeutic protein to a mammalian host are appropriate for treating a mammalian subject having an inherited or acquired disease associated with a specific protein deficiency (e.g., diabetes, hemophilia, anemia, severe combined immunodeficiency). Such protein deficient states are amenable to treatment by replacement therapy, i.e., expression of a protein to restore the bloodstream levels of the protein to at least normal levels.

Alternatively, the mammalian subject may have a condition which is amenable to treatment by expression or overexpression of a protein which is either normally present in a healthy mammalian subject or is foreign to the mammalian subject. The subject methods are also useful to enhance expression of a protein present in a normal mammal, or to express a protein not normally present in a normal mammal, in order to achieve a desired effect (e.g., to enhance a normal metabolic process). The methods are also useful to provide for production of a protein in a cell that is defective in the host.

Methods of Increasing an Immune Response to an Exogenous Polypeptide

The present invention provides methods for eliciting an immune response to an antigen. The methods generally involve administering a recombinant bicistronic flavivirus of the invention to a vertebrate host, wherein the flavivirus enters a host cell, the exogenous polypeptide is expressed independently of the viral proteins, and an immune response is elicited to the exogenous polypeptide.

In some embodiments, recombinant flavivirus as described herein are useful for inducing or increasing an immune response to an antigen in an individual. When the exogenous polypeptide is produced in a vertebrate host, it elicits an immune response to the exogenous polypeptide. In many embodiments, the immune response protects against a condition or disorder caused by or associated with expression of or the presence in the host of, an antigen comprising the epitope. In some embodiments the antigen is a pathogen-associated antigen, and the immune response provides protection against challenge or infection by the exogenous pathogen (bacterial, viral, fungal, parasitic) in which the antigen occurs. Recombinant bicistronic flaviviruses of the invention are, therefore, useful as vaccines (also referred to herein as "immunogenic compositions") to elicit and/or increase an immune response to the antigen. In other embodiments, the antigen is a tumor-associated antigen, and the immune response to the antigen reduces the growth of a cancer cell bearing the antigen, and/or reduces the number of tumor cells bearing the antigen. In other embodiments, the antigen is an allergen, and the immune response to the antigen reduces an allergic response to the antigen. In still other embodiments, the antigen is a sperm-associated antigen, and the immune response to the antigen results in decreased fertility. In still other embodiments, the antigen is one that produces adverse physiological effects in a vertebrate host, and the immune response to the antigen mitigates the adverse physiological effects.

In many embodiments, the exogenous polypeptide is an antigenic polypeptide of a microbial pathogen. Such recombinant flavivirus can then be administered to a host to prevent or treat infection by the pathogen, or to prevent or treat symptoms of such pathogenic infection. Of particular interest in some embodiments is the prevention or treatment of infection or disease caused by microbial pathogens that, during the course of infection, are present intracellularly, e.g., viruses (e.g., HIV), bacteria (e.g., *Shigella, Listeria*, mycobacteria, and the like), parasites (e.g., malarial parasites (e.g., *Plasmodium falciparum*), trypanosomes, and the like), etc. Antigenic polypeptides of such microbial pathogens are well known in the art, and can be readily selected for use in the present recombinant flavivirus vaccine by the ordinarily skilled artisan.

In addition, a recombinant flavivirus of the invention can be used as a delivery vehicle to delivery any antigen to an individual, to provoke an immune response to the antigen. In some embodiments, recombinant flavivirus of the invention are used as bivalent or multivalent vaccine to treat human or veterinary diseases caused by infectious pathogens, particularly viruses, bacteria, and parasites. Examples of epitopes which could be delivered to a host in a multivalent flavivirus vaccine of the invention include multiple epitopes from various serotypes of Group B *streptococcus*, influenza virus, rotavirus, and other pathogenic organisms known to exist in nature in multiple forms or serotypes; epitopes from two or more different pathogenic organisms; and the like.

Suitable subjects include naïve subjects (i.e., subjects who were never exposed to the antigen such that the antigen or pathogen entered the body), and subjects who were previously exposed to the antigen, but did not mount a sufficient immune response to the pathogenic organism.

Whether an immune response has been elicited to a pathogenic organism can be determined (quantitatively, e.g., by measuring a parameter, or qualitatively, e.g., by assessing the severity of a symptom, or by detecting the presence of a particular parameter) using known methods. Methods of measuring an immune response are well known in the art and include enzyme-linked immunosorbent assay (ELISA) for detecting and/or measuring antibody specific to a given pathogenic organism; and in vitro assays to measure a cellular immune response (e.g., a CTL assay using labeled, inactivated cells expressing the epitope on their cell surface with MHC Class I molecules). Whether an immune response is effective to facilitate protection of the host against infection, or symptoms associated with infection, by a pathogenic organism can be readily determined by those skilled in the art using standard assays, e.g., determining the number of pathogenic organisms in a host (e.g., measuring viral load, and the like); measuring a symptom caused by the presence of the pathogenic organism in the host (e.g., body temperature, $CD4^+$ T cell counts, and the like).

In other embodiments, a polypeptide antigen expressed on a given tumor cell (e.g., a tumor associated antigen; "TAA") is inserted into a recombinant flavivirus of the invention as described herein. Such recombinant flavivirus can be administered to an individual having, or suspected of having, a tumor. In some cases, such recombinant flavivirus can be administered to an individual who does not have a tumor, but in whom protective immunity is desired. As is often the case, the immune system does not mount an immune response effective to inhibit or suppress tumor growth, or eliminate a tumor altogether. Tumor-associated antigens are often poorly immunogenic; perhaps due to an active and ongoing immunosuppression against them. Furthermore, cancer patients tend to be immunosuppressed, and only respond to certain T-dependent antigens. In these cases, introduction into the host of a recombinant flavivirus of the invention which expresses an exogenous peptide corresponding to an antigen expressed on the tumor cell surface can elicit an immune response to the tumor in the host.

Any of a variety of known tumor-associated antigens (TAA) can be inserted into flavivirus of the invention. The entire TAA may be, but need not be, inserted. Instead, a portion of a TAA, e.g., an epitope, particularly an epitope that is recognized by a CTL, may be inserted. Tumor-associated antigens (or epitope-containing fragments thereof) which may be inserted into flavivirus include, but are not limited to, MAGE-2, MAGE-3, MUC-1, MUC-2, HER-2, high molecular weight melanoma-associated antigen MAA, GD2, carcinoembryonic antigen (CEA), TAG-72, ovarian-associated antigens OV-TL3 and MOV18, TUAN, alpha-feto protein (AFP), OFP, CA-125, CA-50, CA-19-9, renal tumor-associated antigen G250, EGP-40 (also known as EpCAM), S100 (malignant melanoma-associated antigen), p53, prostate tumor-associated antigens (e.g., PSA and PSMA), and p21ras.

Suitable subjects include subjects who do not have cancer, but are considered at risk of developing cancer; and subjects who have cancer, but who have not mounted an immune response sufficient to reduce or eliminate the cancer.

Recombinant flavivirus comprising a TAA can be administered to an individual as described above. Whether an immune response is elicited to a given tumor can be determined by methods standard in the art, including, but not limited to, assaying for the presence and/or amount of TAA-specific antibody in a biological sample derived from the individual, e.g., by enzyme-linked immunosorbent assay (ELISA), radioimmunoassay (RIA), and the like; assaying for the presence and/or numbers of CTLs specific for a TAA; and the like. Assays for determining the presence and/or numbers of TAA-specific CTLs are known in the art and include, but are not limited to, chromium-release assays, tritiated thymidine incorporation assays, and the like. Standard immunological protocols may be used, which can be found in a variety of texts, including, e.g., Current Protocols in Immunology (J. E. Coligan, A. M. Kruisbeek, D. H. Margulies, E. M. Shevach and W. Strober Eds. 1991).

Whether an immune response is effective in reducing the number of tumor cells in an individual can be determined by standard assays, including, but not limited to, measuring tumor cell mass, measuring numbers of tumor cells in an individual, and measuring tumor cell metastasis. Such assays are well known in the art and need not be described in detail herein.

Using the methods and compositions described herein in connection with the subject invention, an immunoprotective response against microbial infection can be induced in any subject, human or non-human, susceptible to infection by a microbial pathogen, or who has been infected with a microbial pathogen. Where the recombinant flavivirus comprises an exogenous nucleic acid sequence encoding a TAA, the subject may be one that is known to have cancer, is suspected of having cancer, or does not have cancer, but in whom immunity to cancer is to be induced.

Methods for Producing an Exogenous Polypeptide

The invention further provides methods of producing an exogenous polypeptide in a vertebrate host cell. The methods generally involve contacting a recombinant bicistronic flavivirus of the invention with a susceptible host cell, culturing the host cell for a period of time to allow production of the exogenous polypeptide by the host cell. In some embodiments, the methods further comprise purifying the exogenous polypeptide from the host cell or from the culture medium.

In some embodiments, the exogenous protein remains intracellular (e.g., in the cytoplasm, in a cell membrane, or in an organelle), in which case the cells are disrupted. A variety of protocols for disrupting cells to release an intracellular protein are known in the art, and can be used to extract an exogenous protein from a cell. In other embodiments, the exogenous protein is secreted into the medium in which the cells are grown.

In certain embodiments, an exogenous polypeptide is present in a composition that is enriched for the exogenous polypeptide as compared to its naturally occurring environment, or as compared to a starting material comprising the exogenous polypeptide. For example, purified exogenous polypeptides are provided, where by purified is meant that the exogenous polypeptide is present in a composition that is substantially free of proteins other than the exogenous polypeptide, where by substantially free is meant that less than 90%, usually less than 60% and more usually less than 50% of the composition is made up of proteins other than the exogenous polypeptide. An exogenous polypeptide may also be present as an isolate, by which is meant that the protein is substantially free of other proteins and other naturally occurring biologic molecules, such as oligosaccharides, polysaccharides, lipids, polynucleotides and fragments thereof, and the like, where substantially free in this instance means that less than 70%, usually less than 60% and more usually less than 50% of the composition containing the isolated protein is some other naturally occurring biological molecule. In certain embodiments, the exogenous polypeptide is present in substantially pure form, where by substantially pure form is meant at least 95%, usually at least 97% and more usually at least 99% pure.

Any convenient protein purification procedures may be employed, where suitable protein purification methodologies are described in Guide to Protein Purification, (Deuthser ed.) (Academic Press, 1990). For example, a lysate may prepared from the infected host cell, or a cell culture supernatant may be produced, and the exogenous protein purified using HPLC, exclusion chromatography, gel electrophoresis, affinity chromatography, and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations are used, e.g., h, hours; min, minutes; s, seconds; and the like.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Example 1

Engineering Bicistronic Recombinant Yellow Fever Virus

Bicistronic YFV genomes were engineered by inserting at the 3' non-coding region of the YVF genome a fragment of 120 to 700 bp corresponding to the internal ribosomal entry site (IRES) derived from either viral or cellular RNAs. Table 1 provides a list of IRES which were used to generate recombinant YFV. Translation of normal YFV proteins initiates from the 5' capped end of the viral genome, while translation of inserted foreign proteins is directed from the inserted IRES. All of the YFV proteins are correctly produced and viral replication proceeds normally in the recombinant YFV of the invention. The replication characteristics of the recombinant viruses were assessed as well as the levels of antigen expression and genetic stability.

TABLE 1

List of IRES used to construct bicistronic Yellow Fever Viruses

| IRES | Type | Length | Virus (PFU/ml) |
|---|---|---|---|
| Mengo | Viral 2 | 569 nt | $5 \times 10^5$ |
| HCV | Viral 3 | 377 nt | $2 \times 10^6$ |
| Gtx | Cellular | 227 nt | $2 \times 10^5$ |

To produce the YFV constructs, the complete coding sequence corresponding to the YFV genome was cloned into a low copy number bacterial plasmid: pYF-FL. The plasmid can be further manipulated by standard molecular biology techniques to generate the appropriate modification in the YFV genome.

To generate viral genomes containing insertions of foreign sequences, YFV cDNA containing a multiple cloning sites (MCS) of bicistronic YFV cDNA were constructed by overlap PCR. This procedure was followed by obtaining PCR-amplified IRES-elements containing DNA fragments as shown in Table 1 and the cloning of these fragments into the pYF-FL plasmid. Additionally, the firefly luciferase or the green-fluorescent protein gene was also inserted into the pYF-FL plasmid, 3' to the different IRES fragments to construct the following vectors; bYF-M-Luc, bYF-C-Luc, bYF-G-Luc, bYF-M-EGFP, bYF-M-GFP/Zeo. "M" indicates a Mengo IRES; "C" indicates an HCV IRES; and "G" indicates a Gtx IRES. The plasmids were then digested at a unique restriction site present at the 3' end of the genomic cDNA. Subsequent transcription of this DNA template by the SP6 RNA polymerase generated a full length viral RNA which was transfected in permissive cells in order to obtain infectious virus. The recombinant viruses are defined in Table 2.

TABLE 2

| Bicistronic recombinant Yellow Fever Viruses. | | | | |
|---|---|---|---|---|
| Virus | Foreign gene | Gene Length | Genome Length | Virus (PFU/ml) |
| YF-17D | — | 0 nt | 10,861 nt | $1 \times 10^7$ |
| YF-MCS | Linker MCS | 39 nt | 10,900 nt | $1 \times 10^7$ |
| bYF-M-Luc | Luc | 1600 nt | 13,134 nt | $5 \times 10^5$ |
| bYF-M-EGFP | EGFP | 726 nt | 12,204 nt | $2 \times 10^7$ |
| bYF-M-GFP/Zeo | GFP + zeocin | 1077 nt | 12,553 nt | $1 \times 10^7$ |

Example 2

Production of Luciferase by Bicistronic YFV Vectors

Figure 2:
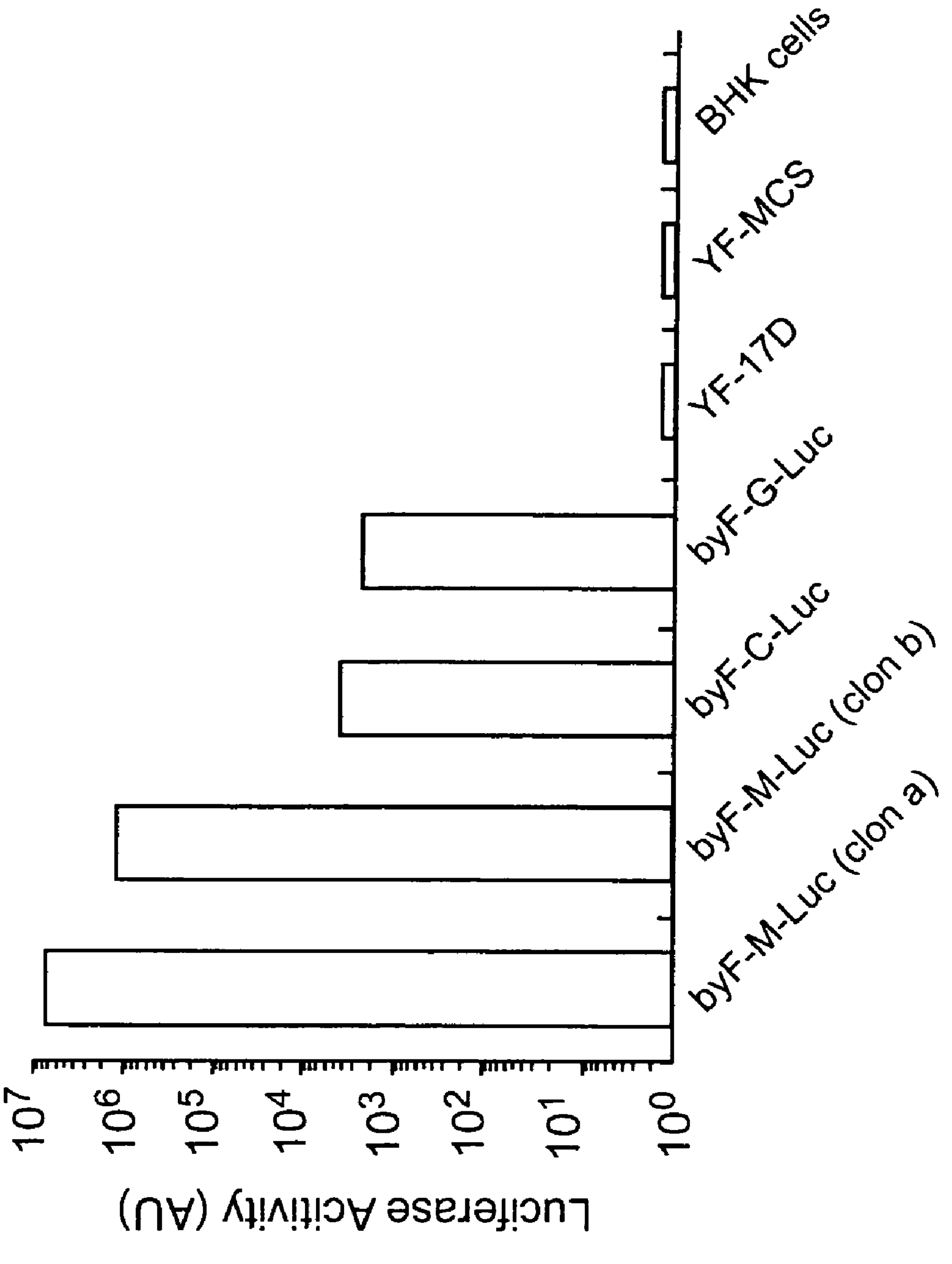
FIG. 2 is a graphical representation of the production of luciferase by bicistronic YFV vectors bYF-M-Luc, bYF-C-Luc, and bYF-G-Luc.
Figure 3:
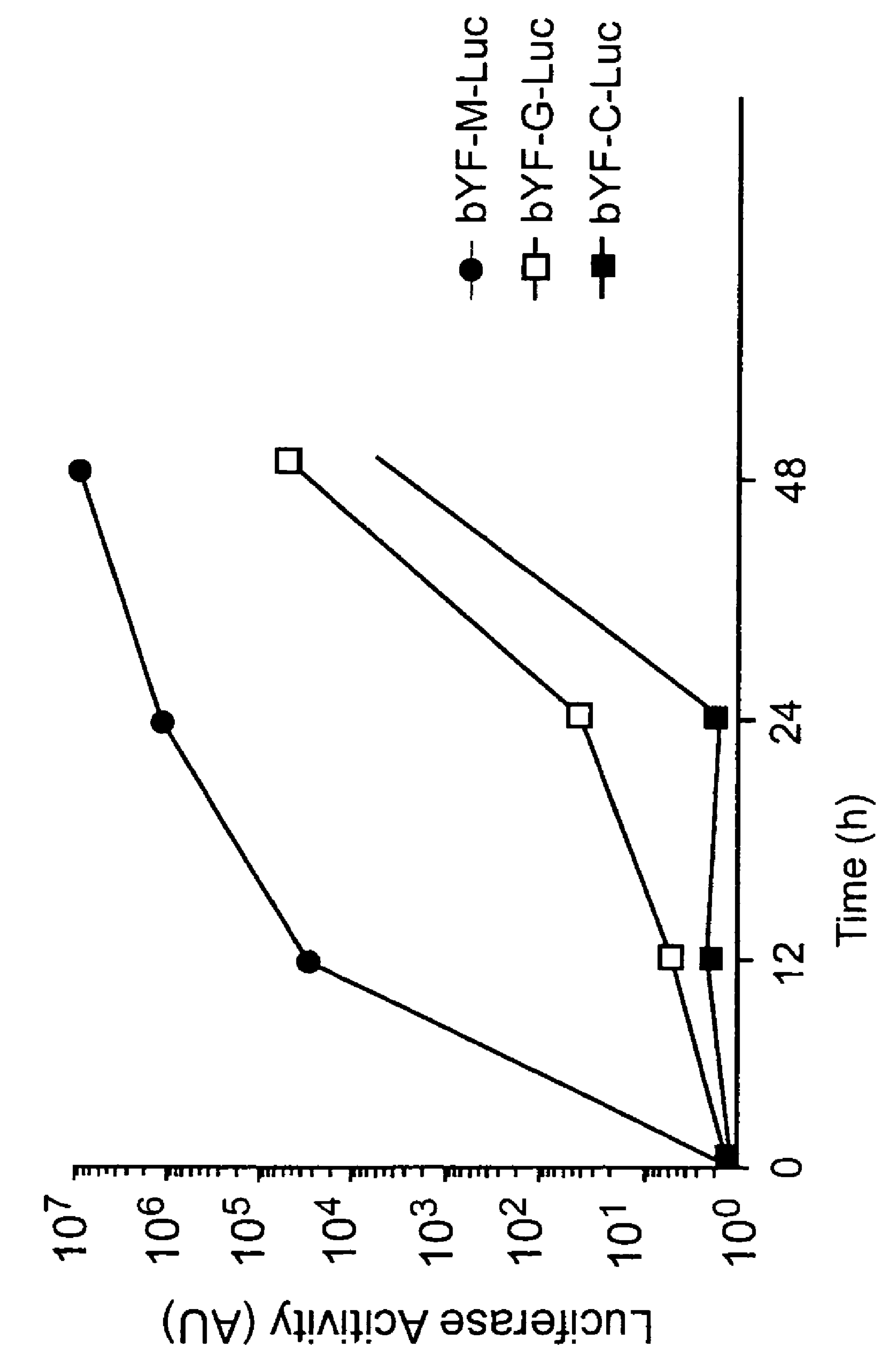
FIG. 3 is a graphical representation of the time course of luciferase production in BHK cells transfected with bYF-M-Luc, bYF-C-Luc, or bYF-G-Luc

Bicistronic YFV vectors containing the luciferase reporter gene were shown to produce luciferase in infected BHK cells. FIG. 2 shows the production of luciferase from BHK cells transfected with recombinant bicistronic viruses (bYF-M-Luc, bYF-C-Luc, and bYF-G-Luc) carrying a luciferase reporter gene, along with the appropriate controls, BHK cells transfected with 17D parental YFV, 17D carrying a Multiple cloning site (MCS) and uninfected cells. Cytoplasmic extracts of the BHK cells were obtained 24 hours post-transfection. Luciferase activity was measured from the extracts by standard techniques and normalized for protein concentration. Transfection of RNA derived from bYF-M-Luc, bYF-C-Luc, and bYF-G-Luc into BHK cells resulted in the production of substantial amount of luciferase activity indicating that the bicistronic YFV recombinant genomes are capable of expression luciferase. FIG. 3 shows graphically the time course of luciferase production in BHK cells following transfection with bYF-M-Luc, bYF-C-Luc, or bYF-G-Luc.

Example 3

Replicative Characteristics of Bicistronic YFV Recombinants

The replicative characteristics of the bicistronic YFV recombinants were analyzed by plaque assay and one-step growth curves. The recombinant viruses carrying the luciferase gene or the enhanced green-fluorescent-proteins (EGFP) have been shown to replicate at rates remarkably similar to wild-type parental strain and also achieve nearly equivalent titers.

Insertion of the entire luciferase gene (1,500 nucleotides in length) downstream of the IRES element yielded viable virus that replicates with a phenotype similar to the parental virus. To analyze the phenotype of recombinant virus, BHK cells were infected with recombinant b-YFV-Luc or parental virus obtained after 1, 2, or 3 passages on tissue culture. The BHK cells were incubated at 37° C. for 4 days. Plaques produced by bYFV-Luc-recombinant resembled those of the parental virus. In addition, high titer stocks of the recombinant virus ($1\times10^6$ to $10^7$ PFU/ml) were obtained.

Figure 4:
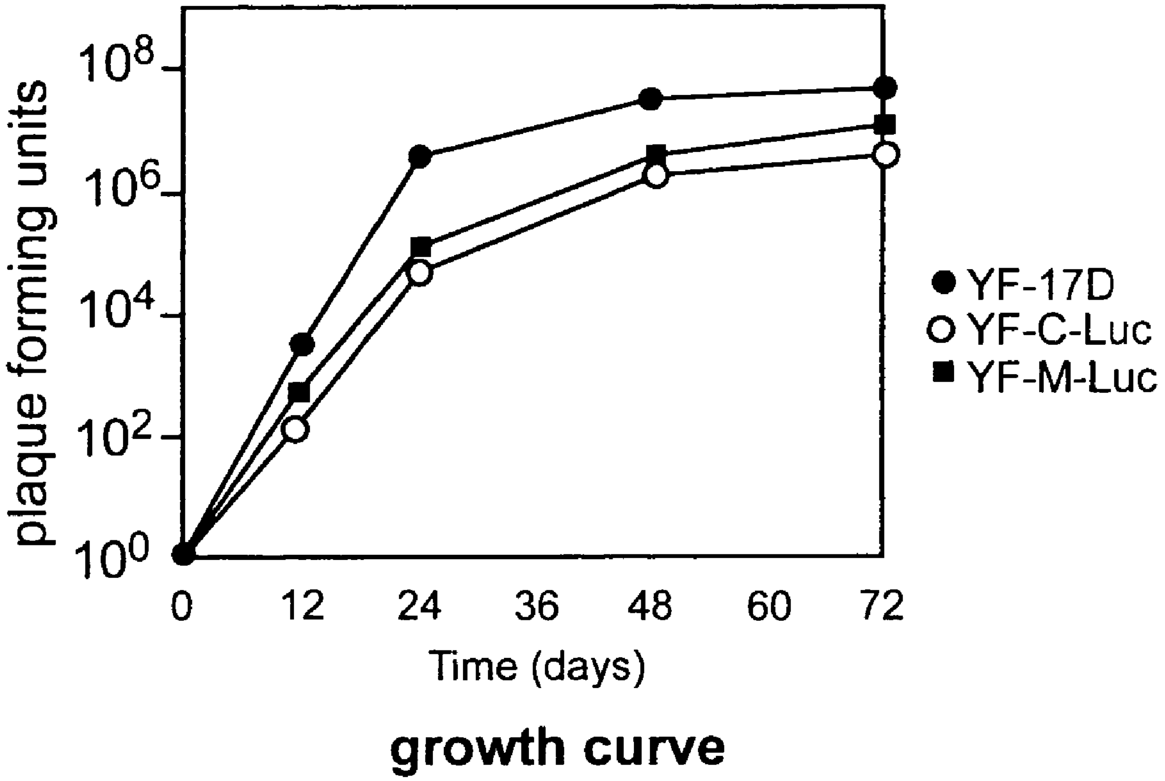
FIG. 4 shows the growth curve of bicistronic YF viruses expressing luciferase.

FIG. 4 also demonstrates the similar replicative characteristics of the bicistronic YFV recombinants to wild-type viral strains. FIG. 4 is a graphical representation of the one-step growth curves of parental yellow fever 17D strain (YF-17D) and three bicistronic YF recombinant viruses: bYF-M-Luc, and bTF-C-Luc. A similar growth pattern is seen for wild-type YF and all three recombinant viruses in FIG. 4.

RNA viruses exhibit a high rate of genetic variation (point mutations, recombination, etc.) which can affect the immunogenicity of the vaccine. The genetic stability of the sequences inserted into the YFV genome was carefully examined for possible genetic variations. To identify genetic variation, recombinant viral stocks were generated by sequential passages in BHK cells followed by RT-PCR analysis of the YFV genome. The original genetic structure of the YFV was retained after 3 passages in BHK cells, as shown by RT-PCR analysis of BHK cells infected with recombinant bYF-M-Luc after three rounds of replication, and BHK cells infected with parental 17D virus. The presence of the foreign sequence was analyzed by RT-PCR of total cytoplasmic RNA from infected cells.

Example 4

Production of Fluorescence by Bicistronic YFV Recombinants

Fluorescent bicistronic YFV recombinants were constructed by amplifying full length EGFP or GFP/Zeo fusion (enhanced green fluorescent protein and green fluorescent protein fused to antibiotic zeocin) from pEGFP and pGFP/Zeo (Clontech, CA), and then cloning these PCR fragments into the NotI and PmeI sites of pbYF-M-Luc by standard techniques. The constructs containing the EGFP and GFP/Zeo sequences were named bYF-M-EGFP and bYF-M-GFP/Zeo, respectively.

Upon transfection of bYF-M-EGFP or bYF-M-GFP/Zeo viral RNA into BHK cells, GFP was expressed to high levels in all cells positive for YFV proteins. YFV protein was detected using a mouse hyperimmune anti-total YFV proteins antibody that had ban conjugated to Alexa 594 (a bright, Texas Red-like fluorophore) (Molecular Probes, OR; Alexa 594 Protein Labelling Kit). BHK cells infected with bYF-M-EGFP for 48 hours were fixed and permeablized (CalTag, Ca) in the presence of 0.5 ml Alexa 594 fluorescently labeled anti-YFV antibody in a 50 ml total volume. Stained cells were visualized for immunofluorescence using a Leica DMLB microscope.

The percentage of cells positive for both GFP and YFV proteins was also examined. To determine the percentage of GFP+ virus in a viral stock, bYF-M-EGFP was plaque assayed and GFP+ plaques were visualized, using a long-pass FITC filter, as a green circle of cells. A high percentage of cells stained positive for both GFP and YFV.

The viability and stability of recombinant YFV containing SIV sequences were also examined. A modified bYF-M-EGFP containing SIV sequences was shown to maintain the SIV sequences for at least six passages by double staining experiments.

These experiments clearly demonstrate that bicistronic yellow fever viruses are capable of expressing a substantial amount of foreign proteins and retaining the inserted sequences for a large number of rounds of replication.

Example 5

In vivo Analyses

Methods

Construction of Recombinant Plasmids

A plasmid encoding the complete YF-17D sequence was used. Bicistronic vectors were constructed by inserting sequences at the 3' noncoding region of the genome. To facilitate cloning, we used a primer extension approach to insert a multiple cloning site (AscI, PacI, PmeI, and SnaBI) exactly 25 nucleotides downstream the end of the yellow fever open reading frame (ORF). Next, we PCR-amplified IRES-containing DNA fragments and cloned those fragments into pYF-17D. Finally we cloned the firefly luciferase gene after several different IRES to obtain the plasmids: bYF-Cyr61-Luc, bYF-Gtx-Luc, bYF-HCV-Luc, b-YF-BVDV-Luc, bYF-Mengo-Luc, bYF-Polio-Luc. Constructs bYF-Mengo-eGFP and bYF-Mengo-GFP/Zeo were made by amplification and cloning of full length eGFP or GFP/Zeo fusion from peGFP and pGFP-Zeo plasmids (Clontech, Palo Alto, Calif.) respectively, into the NotI and Pmel sites of bYF-Mengo-Luc plasmid (FIGS. 5A-D).

DNA Sequencing

All sequencing reactions were performed on an ABI Prism® 310 DNA Genetic Analyzer (Applied Biosystems, Foster City, Calif.). We applied Megalign software (DNA Star Inc., Madison, Wis.) for computer-aided analysis of sequence data.

Generation of Viruses from Plasmids

In all cases the viral cDNA were digested with Xho I and used as templates for in-vitro transcriptions driven by the SP6 RNA polymerase in the presence of 7-methyl guanosine cap-structure (mMessage mMachine, Ambion, Austin, Tex.), Transcription products were treated with DNAse for 15 minutes at 37° C., and precipitated with ethanol/7.5 M ammonium acetate. The concentration of RNAs was estimated by spectrophotometry. Since XhoI is not a unique site in the bYF-BVDV-Luc and bYF-Mengo-GFP/Zeo constructs, a partial digestion with XhoI was carried out in order to generate full-length linearized cDNAs. The RNAs were transfected into BHK-21 cells by electroporation using 2.5 ug of RNA per $2\times10^6$ cells on an electro cell manipulator 600 (BTX, San Diego, Calif.).

Cell Lines

BHK-21 cells were used to make the viral stocks, plaque assay and growth curves; and COS were used for the IF experiments.

Viral Stocks

Cytopathic effect (CPE) was observed 3 to 5 days following transfection. Supernatants of transfected cells were collected after 3 days, cleared, aliquoted, titered and stored at −70° C.

Single-Step Growth Curves

Subconfluent BHK-21 cell monolayers were washed once with PBS and infected at a multiplicity of infection (MOI) of 5 PFU/cell. After a 1 hr incubation period at 37° C., the cells were washed twice with PBS and then covered with MEM with Earle's BSS medium supplemented with 10% Fetal Calf Serum. Infected cell cultures were incubated at 37° C. and aliquots were recovered every 12 hours for a period of 3 days. Titers were determined by plaque assay. Briefly, serial dilutions of viral aliquots were made and added to BHK cell dishes for 1 hour to allow viral adsorption, plates were washed once with PBS before adding 1× MEM and 0.8% agar overlay, plaque assays were then incubated at 37° C. for 5 days. Agar overlays were then removed, and plates were stained with vital dye (0.1% crystal violet, 20% ethanol) to reveal viral plaques, which were counted.

Analysis of Viral RNA by RT-PCR

After several passages of recombinant viruses on BHK-21 cells, total cytoplasmic RNA was obtained from infected cells using TRIZol following manufacturer's protocol (Life Technologies, Rockville, Md.). Next, reverse transcription was carried out using Superscript II (LifeTechnologies, Rockville, Md.), with random hexamers, 1 ul of cDNA was added as template in a PCR reaction using rTth (PE Biosystems, Foster City, Calif.) and specific flanking primers for each case.

Analysis of Viral RNA Replication by Real Time RT-PCR

HBK cell monolayers were infected with equal concentration of virus (MOI=5) and total cellular RNA was extracted at different times to quantified the replication of viral RNA.

Immunostaining (Immunocyto/Histochemistry)

Cells were plated on glass cover slips and allowed to attach overnight ($1\text{-}5\times10^4$ cells/cover) (Fisherbrand, Pittsburg, Pa.). Infections were carried out for one hour at 370 C, cells were washed with PBS before adding media and then placed at 37° C. for 2-3 days. Subsequently, cells were washed with PBS and fixed in 4% paraformaldehyde (PFA) for 10 minutes. After washes incubation with primary antibodies in PBS buffer containing 0.1% Triton X-100, 2% NCS and 0.02% Sodium azide, Yellow Fever (17D) hyperimmune ascitic fluid (mouse) (National Institute Allergy and Infectious Diseases, Maryland, cat# V525701-562) or IgG fraction of a rabbit anti-Luciferase antiserum (SIGMA, St. Louis, Mo., cat#L-0159) was performed for one hour at room temperature. Cells were rinsed three times for 10 minutes with agitation with PBS and 0.1% Triton X-100 (Bio-Rad Laboratories, Hercules, Calif.). FITC and TRITC-conjugated secondary antibodies (Jackson ImmunOResearch Laboratories, West Grove, Pa.) were incubated for 30 minutes at room temperature, protected from light. Finally cells were rinsed three times for 10 minutes and mounted in Vectashield medium with DAPI (Vector Laboratories, Burlingame, Calif.).

Luciferase Assay

Cell monolayers were washed once with PBS and scraped-off the plate. Extracts were prepared using 100 ul of cell culture lysis reagent (CCLR), (Luciferase Assay System, Promega, Wis.). Ten μl of the extract were placed in an Opto-compI automated luminometer (MGM Instruments, Hamden, Conn.).

Luciferase Expression in Viral Plaques in Real Time

After an incubation of 6 days at 37° C., the agar overlay was removed and the luciferase substrate (luciferin) was added. The luciferase activity was measured with a equipment that detect the photons emitted by the luciferase that is being translated in the infected cells and is visualized with colors that indicate the level of luciferase activity. Images of the expression were taken and the plaques were observed after developing with crystal violet.

Bicistronic YF-Mengo-eGFP Stability

Stock YF-Mengo-eGFP P0 was produced after transfection of BHK cells with in vitro RNA and incubation for 3 days at 37° C. Future passages consisted in infection of BHK monolayers at low MOI (MOI=0.01) and incubation for periods of 3 days to generate new viral stocks, namely P1-P5. Plaque phenotype was study by direct observation under fluorescence microscope before the staining with crystal violet. Plaques expressing eGFP were identified and the phenotype observed was compared with plaques that did not express eGFP. Each viral stock was used to infect new BHK monolayers and after a 48-hour period the total RNA was extracted and used as template for RT-PCR to detect the eGFP sequence.

Expression of eGFP After Cellular Passages Assessed by Quantitative Immunofluorescence The same condition was used to infect cells with the different passages. The percentage of infected cells that express eGFP was determined for each viral passage. Yellow fever viral proteins were detected using mouse anti-YFV antiserum and, as a secondary antibody, anti-mouse IG antibody conjugated with TRITC (red fluorescence).

Processing of Mice Tissues for Cryostat Slides

Various tissues were extracted from perfused mice to make cryostat slides. The tissues were treated with sucrose 15% (for 3 hours) followed by sucrose 30% (for 1 hours). The tissues were embedded in OCT (Tissue-Tek OCT compound, Sakura, Calif.) for 10 minutes and were frozen in new OCT and kept at −70° C. The slides were made in cryostat, placed in glass charged to favor tissue adhesion and kept at −700 C until immunohistochemical staining.

Immunohistochemistry of Mouse Tissues

The tissues were rehydrated in PBS for 10 minutes, and then were placed in a solution to block unspecific binding of antibodies for one hour at room temperature. The primary antibody was incubated at 4° C. over night. The primary antibodies were: Yellow Fever (YF17D) or IgG fraction of rabbit anti-luciferase antiserum. The second day the slides were washed 3 times in PBS for 10 minutes with shaking. The secondary antibodies were conjugated with FITC, TRITC, or Texas red (Jackson ImmunOResearch Laboratories, West Grove, Pa.) and were incubated for 2 hours at room temperature, protected from the light. Finally, the slides were washed 3 times for 10 minutes, and were incubated with a solution containing DAPI before mounting for the microscopic visualization in Vectashield medium (Vector Laboratories, Burlingame, Calif.).

Luciferase Detection In Vivo

The mice were anesthetized with pentobarbital (70 mg/kg). A solution of the substrate luciferin (50 mM; 12 mg/Kg., Molecular Probes, Eugene, Oreg.) was injected in the peritoneal cavity 10 minutes before the image was taken. The mice were then placed in a dark box. An image with fluorescent white light was taken as reference using a photographic camera with Nikon lenses. A computerized system coupled with the camera was used to analyze the images.

The luciferase translated inside the animal produced emission of photons that were transmitted through the tissues, collected and integrated for a period of 10 minutes. An image in colors representing the light intensity (blue for the less intense and red for the most intense) was generated by a processor of images Aarhus 20 (Hamamatsu, Bridgewater, N.J.) and were transferred using a module coupled with a computer with an image processor (Photoshop, Adobe Systems, Mountain View, Calif.). The images of reference were superimposed on the color images and the annotations were realized using software for graphics.

Results

The viral vectors are based on the vaccine strain YF17D. The recombinant viruses carry and express large exogenous sequences (2,358 nucleotides). The insertions are placed downstream the ORF of the YFV genome. Several cellular and viral internal ribosome entry sites (IRES) drive the expression of foreign genes. In this report, we describe the design and use of a bicistronic vector system into which the IRES of two picornavirus (Mengo virus (MV) and poliovirus (PV)) a pestivirus (BVDV) and an hepacivirus (HCV), have been inserted into the intercistronic spacer to drive luciferase protein synthesis (FIGS. 5A-D). The sequences required for internal initiation of translation extend at least up to the authentic viral initiation codon in the case of the Mengo virus IRES, and BVDV IRES, and beyond it in the case of HCV. Thus, internal initiation of translation results in the synthesis of luciferase protein with N-terminal extensions of 7, 4 and 11 amino acids respectively (FIGS. 5A-D). Similarly, although the 3' boundary of the polio IRES lies upstream of the authentic initiation codon for ease of construction the 5'-UTR fragment used extends beyond the authentic viral AUG codon, thus poliovirus IRES activity results in the synthesis of a luciferase protein which has an N-terminal extension of three amino acids (FIGS. 5A-D).

Comparison of IRES Efficiencies in Transfected Cells

Transfection of in vitro synthesized RNA derived from constructs bYF-Cyr61-Luc, bYF-Gtx-Luc, bYF-HCV-Luc, bYF-BVDV-Luc, bYF-Mengo-Luc, and bYF-Polio-Luc into BHK cells resulted in the production of substantial amounts of the reporter gene, as measured by luciferase activity assays. The mengo IRES was the most efficient in driving downsteam cistron translation, followed by the BVDV and Polio IRES, which were 7 and 17 fold less efficient than the Mengo IRES respectively. The cellular IRES (Cyr61 and Gtx), and HCV IRES were much less efficient in directing internal translation initiation (more than 300 fold difference with the Mengo IRES). When luciferase activity was measured 2 and 3 days post-transfection, all constructs showed increased expression over time, after this period the virus cause cytopathic effect to the cells.

Replication of Bicistronic YFV Recombinants

In order to assess the efficiency of replication, plaque assays were carried out, showing that all recombinants carrying the luciferase gene or the enhanced green-fluorescent-proteins (eGFP) generate infectious viruses in high titers ($10^6$ to $10^7$ pfu/ml).

One Step Grow Curve

Using the high titer stocks, BHK monolayers were infected and incubated at 37° C., cell suspension samples were taken at different time points and were titered by plaque assay. A growth curve was plotted showing that some viruses (bYF-Gtx-Luc, bYF-Polio-Luc, bYF-Cyr61-Luc bYF-HCV-Luc) are produced at low levels at early time points (24 to 48 hours post infection) in comparison with the virus YF17D and other bicistronic viruses (bYF-Mengo-Luc, bYF-BVDV-Luc). After a longer incubation (48 to 72 hours post infection) all the bicistronic viruses reached the level of replication shown for YF-17D.

Analysis of the Insert Retention by Studying the Replication of the Viral RNA in the Infected Cell Utilizing Kinetic RT-PCR Although all the recombinant viruses are capable of replication from cell to cell yielding high titers, we do not have information if the virus we titer maintained the insert in their genome. To answer this question, we analyzed the replication of the bicistronic genomes in the infected cell by quantitative amplification. For this reason we extracted RNA at different time points after infection (MOI=5 pfu/cell). The time after infection at which RNA was collected was extended more than the expected cytopathic effect time for YF17D, because of the possibility that the recombinant viruses could replicate slowly, and the time of appearance of cytopathic effect could be modified. The extracted RNA was quantified and used as template for the real time RT-PCR. Specific primers for the YF genome (complementary to the ORF of YFV) and for the inserted sequence (luciferase) were used. Samples were processed by duplicates for each set of primers, and a constitutively expressed gene (hamster GAPDH) was amplified as internal control to ensure that the amount of total RNA used as template was uniform.

Amplification curves of YF and luciferase were plotted for each bicistronic YFV. The bicistronic virus bYF-gtx-Luc retains the insert during the period analyzed, which amplification curves for the viral sequence and the luciferase sequence were nearly identical to each other over the time analyzed. Positive real time RT-PCR was obtained for every bicistronic virus Luc indicating that the insert was maintained during replication.

Yellow Fever Proteins Detected in Cultured Cells by Immunohistochemistry

BHK and COS cells were infected at low MOI (MOI=0.01 pfu/cell) and processed for immunostaining to detect YF infected cells. After two days of incubation positive cells for the YF proteins were detected. To determine stability of the inserted sequences, bYF-Mengo-Luc was passed on BHK cells several times and then expression of luciferase determined by immunohistochemistry. About 75% of the infected cells retained luciferase expression after 5 passages in BHK cells.

Analysis of the Expression of Luciferase in Infected Cells by Double Immunohistochemistry To evaluate the expression of luciferase by the various bicistronic viruses, BHK cells were infected with bYF-Mengo-Luc and bYF-Polio-Luc. After 2 days of incubation, the presence of luciferase was detected by double immunohistochemistry. The presence of YFV proteins was detected using, as primary antibody, mouse YFV-specific antibodies (anti-YF), and, as secondary antibodies, anti-mouse Ig conjugated with FITC (green fluorescence). Luciferase was detected using, as primary antibody, rabbit luciferase-specific antibodies, and, as secondary antibodies, anti-rabbit Ig antibody conjugated with rhodamine (red fluorescence). Cells expressing yellow fever proteins exhibit green fluorescence; and cells expressing luciferase exhibit red fluorescence. The results demonstrate that luciferase expression is detectable in infected cells.

Quantitative Assessment of the Expression Levels of the 2$^{nd}$ Cistron

The ability to express luciferase after infection was tested in a quantitative assay. High-titer viral stocks of bicistronic YF-Luciferase recombinants were produced in BHK cells. To confirm whether the recombinant viruses were infectious and able to express the inserted sequences, BHK cells were infected with the same titer of all viruses, and cell extracts were prepared at different time points after infection to determine the luciferase activity. Luciferase was readily detected after 12 hours post infection and increased exponentially over time up to 48 hours. Bicistronic viruses containing cellular IRES (bYF-Gtx-Luc, and bYF-Cyr61-Luc) and HCV IRES (bYF-HCV-Luc) showed low levels of expression, and the rest of the viruses (bYF-Polio-Luc, bYF-Mengo-Luc y bYF-BVDV-Luc) showed at least two fold higher levels. This observation indicates that the YFV genome can accommodate at least 2,358 additional nucleotides and that the foreign sequences are retained for a number of passages.

Analysis of the Plaque Morphology

Upon infection of subconfluent BHK cells, YFV and YFV-MCS produce characteristic large and clear plaques. Conversely, bYF-Mengo-Luc, bYF-BVDV-Luc, bYF-Gtx-Luc, and bYF-HCV-Luc display smaller and blurred plaques. The appearance of scattered big plaques might indicate that the insert is being lost at different rates in each revertant species.

In addition, infection with 5-10 p.f.u. per cell of virus (every 12 h virus was harvested and titered on BHK-21 cells to obtain a single step growth curve) indicated that recombinants replicate at rates remarkably similar to those of the parental strain 17D, achieving nearly equivalent titers.

Analysis of Viral Plaques Expressing Luciferase in Real Time

After infection with recombinant YF carrying luciferase, BHK cells were overlaid with agar to favor plaque formation. Using equipment that allows the detection of light emitted by the cells, we were able to see the infected cells that express luciferase. After adding the specific substrate, all the bicistronic viruses that contain luciferase gene showed enzymatic activity and emitted detectable light. This suggests that all of the bicistronic viruses express efficiently the enzyme and that the biological activity is maintained.

The viruses can be divided in two groups, one group of viruses expresses low levels of luciferase, and includes those containing cellular IRES and the HCV (bYF-Gtx-Luc, bYF-Cyr61-Luc and bYF-HCV-Luc); the second group includes viruses containing viral IRES that express high levels of luciferase (bYF-Polio-Luc, bYF-Mengo-Luc y bYF-BVDV-Luc). Viral plaques are opaque and smaller in size when the virus expresses luciferase. Clear and bigger plaques are indicative of viruses not expressing luciferase. 93% of bYF-Gtx-Luc virus and 92% of bYF-BVDV-Luc express luciferase. It is notable that these two groups of viruses agree with the ones described before, based on the luciferase activity from cellular extracts.

The cells that were infected with highest concentration of virus bYF-Mengo-Luc and bYF-Polio-Luc show a total cytopathic effect at the time of data collection impairing the visualization of the expression of luciferase. Whereas the same wells infected with the viruses bYF-BVDV-Luc, bYF-cyr-Luc and bYF-gtx-Luc do not show evidence of total cytopathic effect after 6 days, and the luminous plaques were clearly visible.

Because the half-life of luciferase is approximately 2 hours, the enzyme detected during the analysis was likely synthesized within a 2-hour period before the assay In this assay, plaques with different sizes and opacity could be observed. By comparing plaques obtained by the classic plaque assay (developed with crystal violet), one can distinguish between plaques that express high levels of luciferase and plaques that express lower levels or do not express luciferase. The vast majority of the plaques of the virus bYF-Gtx-Luc (93%) and with the virus bYF-BVDV-Luc (92%) express luciferase.

Insert Retention in the bYF-Mengo-eGFP Viral Genome

RNA viruses exhibit a high rate of genetic variation (point mutations, recombination, etc.). Since this may affect the immunogenicity of the vaccine we decided to examine the genetic stability of the eGFP sequence inserted into the YFV genome. To this end, we generated viral stocks by sequential passages in BHK cells with an MOI of 0.01, taking the supernatant after 3 days and analyzing YFV genome by plaque assay, RT-PCR, and immunocytochemistry.

All plaques produced by bYF-Mengo-eGFP were small and clear, indicating a slower replication and the presence of the insert.

By analyzing the plaque morphology we can infer that the insert is lost after the passages, more remarkably after the 3$^{rd}$ passage. To confirm this result at the level of a single Yellow Fever infected cell, we checked the amount of cells expressing the EGFP by immunocytochemistry.

The presence of eGFP RNA in the bYF-Mengo-eGFP genome was analyzed after successive passages in cultivated cells. The results show that after P5, the presence of RNA genomes containing the eGFP gene is detectable. However, this technique does not indicate whether the gene is functional, since small mutations or even deletions are not detected by RT-PCR analysis.

Bicistronic Virus YF-Mengo-eGFP Stability

Transfection with in vitro synthesized RNA from plasmids bYF-Mengo-eGFP and bYF-Mengo-GFP/Zeo resulted in the production of substantial amounts of fluorescence which was easily detected visually under a microscope.

To determine the percentage of viruses expressing eGFP (eGFP+) in the viral stocks, bYF-Mengo-eGFP virus was plaqued and cells were observed directly under the fluorescence microscope through the plastic by inverting the dish. All the plaques produced by the bicistronic virus bYF-Mengo-eGFP using the stocks P0 to P2 expressed the fluorescent protein. The passage #P3 showed few bigger plaques that do not express eGFP, as viewed under the microscope.

Study of the eGFP Expression After Passages of the Virus b YF-Mengo-eGFP by Quantitative Immunofluorescence The stability of the virus bYF-Mengo-eGFP was assessed after passages in BHK cells. After passage 3 the virus bYF-Mengo-eGFP is unstable and the percentage of positive cells infected with YF that express eGFP diminished (60% of the infected cells express eGFP). In passage 5 only 10% of the infected cells express eGFP. Since the incubation time necessary to observe the positive sign by immunohistochemistry is reached after 3 days of incubation, at this period all the cells were infected. However, the fluorescence intensities resulted in variability due to the fact that not all the cells were infected at the same time.

Selection of Recombinant bYF-Mengo-eGFP with Enhanced Insert Retention Capacity.

We have selected viruses by FACS sorting eGFP positive infected cells that are capable to produced bigger plaques and retain the inserted sequences for more rounds of replication. BHK cells were infected with bYF-Mengo-GFP and after 24 hours post infection green cells were sorted. At each of round of replication, those cells expressing high levels of GFP were selected. Viruses isolated from "green" cells were used to infect BHK cells to obtained a viral stock of each passage. The selection procedure was repeated 9 times to obtain viral stock named SP1 to SP45. At 24 hours post infection, SP45 selected viruses expressed much higher levels of GFP than parental SP1 viruses. Importantly, selected SP45 virus present a larger plaque phenotype, replicate to higher titers and retained the insert for more than 9 rounds of replication in tissue culture. These experiments indicate that recombinant yellow fever can be isolated that present better replication and insert retention properties.

Detection of Yellow Fever Virus After Intracerebral Inoculation with bYF-Mengo-eGFP The characterization assays in tissue culture of bicistronic viruses containing the reporter gene luciferase showed that the virus containing the IRES derived from Mengo virus belongs to the group of higher expression of the reporter gene. For this reason, bYF-Mengo-eGFP was used in the experiments in mice that are described below. gPVR mice six weeks old were injected IC (intracerebrally) with $10^5$ pfu of bYF-Mengo-eGFP. Six days post infection the brains were extracted and processed for the detection of the presence of the yellow fever virus.

To detect the presence of genomic RNA containing the inserted sequence, RT-PCR using templates of total RNA from brains was extracted. Virus was extracted from brains and was plated to analyze the phenotype recovered. To detect the presence of viral proteins and eGFP, cryostat slides were processed for immunohistochemistry.

RT-PCR from RNA Extracted from Brain of Mice After Intracerebral Inoculation with the virus bYF-Mengo-eGFP To evaluate the presence of viral RNA as well as the retention of the insert in the genome, RNA was extracted from brains of mice infected intracerebrally with the bicistronic viruses. We performed RT-PCR to detect the presence of viral RNA in the brain samples. The RT-PCR for YF shows that both the genome of the virus YF17D and the bicistronic bYF-Mengo-eGFP replicate in the nervous tissue, and viral genomes were detectable 6 day after the IC injection. The RT-PCR for eGFP shows that viral RNA that contains the insert sequence of eGFP is detectable 6 days after the IC injection of mice with the virus bYF-Mengo-eGFP. A fragment that corresponds to the actin gene was apmplified as control that is found in all RNA used as templates from the brain samples (either with or without infections). A fragment of the virus YF17D present in both the parental strain and in the construct bYF-Mengo-eGFP was also amplified. In both controls the results were as expected.

Immunohistochemistry of Mouse Tissue

To study the presence of viral proteins in the brains of infected mice, we performed immunohistochemistry on brains extracted after injection with the viruses YF17D and bYF-Mengo-eGFP. Brains from uninfected mice were processed as controls. The brains were extracted at different time points after the IC inoculation using different viral stocks and different amount of virus. The cells infected with the YFV were detected with specific red fluorescence in the slides of brains obtained after the infection with the parental virus YF17D and with recombinant virus bYF-Mengo-eGFP. The slides were observed under the fluorescent microscope to detect the expression of eGFP. Direct green florescence was not detected in the processed tissues. Extractions were made at different days post-injection.

In every case, eGFP expression was detected. To explore the possibility that the levels of expression of eGFP were insufficient to detect the direct fluorescence under the microscope, specific anti-GFP antibodies were used. The expression of eGFP was not detected, either by direct fluorescence or by immunohistochemistry using specific antibodies. For a complete inspection cryostat slides were made in the coronal plane and in the horizontal plane y horizontal. The absence of signal for eGFP suggested that the construct bYF-Mengo-eGFP does not express the second cistron in a stable way. This observation agrees with the plaque assay using the virus recovered from brains of mice infected with the same virus bYF-Mengo-eGFP, which does not express eGFP and shows the same size as the plaque-generated with the parental YF17D.

Assessment of Luciferase Expression in Mice Tissues

Six week old BALB/C mice were injected IC with the bicistronic virus: bYF-Polio-Luc, bYF-Mengo-Luc and bYF-BVDV-Luc. As negative controls, mice were injected with YF17D and PBS. After 2, 3 or 6 days post-infection brain homogenates were made and the luciferase activity was measured. In the first attempt, whole brain extracts were made in which no luciferase activity was detected. One of the explanations is that the enzyme activity it is diluted in the extract of the whole brain. It may be necessary to obtain homogenates from regions close to the IC inoculation site of the virus to detect luciferase activity, so that the enzyme is concentrated in the site of the inoculation. To avoid the dilution of the expressed protein, four sections of the infected brains were processed independently. All the bicistronic viruses showed luciferase activity in the extracts of brains at different days after the IC inoculation. Significant levels of luciferase were detected in the brains of mice injected via IC after 2, 3 and 6 days after the infection with the bYF-BVDV-Luc; after 2 and 3 days with the virus bYF-Polio-Luc, and only after 2 days with the virus bYF-Mengo-Luc.

Detection of Luciferase Expression in Live Mice

Utilizing a non-invasive method, it is possible to detect the enzymatic expression of luciferase in live mice. The light it is transmitted trough the tissues, and bioluminescence is used to monitor (externally and in a quantitative manner) the expression of the luciferase enzyme in mice. This is a sensitive and quantitative model that provides an analysis in real time of the expression of the enzyme and facilitates monitoring of individual animals. Using this technology, without the need to sacrifice the mice, the bicistronic viruses that contain the luciferase gene were injected into mice to study the activity of luciferase in vivo. The light produced by the infected cells is transmitted through the anesthetized mice. In this experiment, 20 mice were injected via IV, IP and IC. Images were taken after the injections with each route of inoculation, the IC inoculation showed high levels of expression of luciferase when using the virus bYF-polio-Luc ($6.6\times10^5$ total counts).

Based on the previous results, we used IV inoculation for new experiments with the objective to follow the kinetics of expression of the second cistron. The results showed that in 3 out of 5 mice infected with the virus bicistronic bYF-Polio-Luc, the maximum expression is reached at 5 days after the injection and the amount of signal comes from the hepatic region. Similar results were obtained in 2 out of 3 mice injected with the virus bYF-Mengo-Luc and in 1 out of 5 mice infected with the virus bYF-BVDV-Luc. In the mice used as controls, no significant expression of luciferase was detected.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A live, replication-competent, recombinant, attenuated yellow fever virus (YFV), comprising, in order from 5' to 3', a 5' untranslated region (UTR) from a parent YFV, an open reading frame (ORF) encoding all viral proteins of the parent YFV, an internal ribosome entry site (IRES), an exogenous nucleic acid insert that encodes a polypeptide other than a polypeptide encoded by the parent YFV, and a 3' UTR from the parent YFV, wherein the recombinant YFV is capable of propagating in a mammalian host, and wherein the parent YFV is strain 17D, and wherein the nucleic acid insert is retained for at least three passages of the recombinant YFV.

2. The recombinant YFV of claim 1, wherein infection of a host cell with the recombinant YFV provides for expression of the exogenous nucleic acid in the host cell and production of the polypeptide encoded by the exogenous nucleic acid.

3. The recombinant YFV of claim 1, wherein the exogenous nucleic acid comprises a nucleotide sequence that encodes a polypeptide from a pathogenic agent other than the parent YFV.

4. The recombinant YFV of claim 1, wherein the exogenous nucleic acid comprises a nucleotide sequence that encodes a tumor antigen.

5. The recombinant YFV of claim 1, wherein the exogenous nucleic acid comprises a nucleotide sequence that encodes a therapeutic polypeptide.

6. A method of delivering a polypeptide to a host, the method comprising introducing a recombinant YFV of claim 1 into a host that is susceptible to infection with a flavivirus, wherein infection of a host cell with the recombinant YFV provides for expression of the exogenous nucleic acid in the host cell and production of the polypeptide encoded by the exogenous nucleic acid.

7. The method of claim 6, wherein the polypeptide is associated with a microbial pathogen other than the parent YFV.

8. The method of claim 6, wherein the polypeptide is a tumor antigen.

9. The method of claim 6, wherein the polypeptide has therapeutic activity.

10. The method of claim 6, wherein the polypeptide is exported to the host cell surface.

11. The method of claim 10, wherein the polypeptide is presented on the surface of the host cell with a major histocompatibility antigen.

12. The method of claim 6, wherein the polypeptide is secreted from the cell.

13. The method of claim 6, wherein the polypeptide remains in the cytoplasm of the cell.

14. A pharmaceutical composition comprising a recombinant yellow fever virus (YFV) of claim 1; and a pharmaceutically acceptable excipient.

15. A method for eliciting an immune response to a polypeptide antigen in a mammalian subject, the method comprising administering a recombinant yellow fever virus (YFV) of claim 1 to the mammalian subject, wherein the recombinant YFV encodes a polypeptide antigen, wherein infection of a cell of the subject with the recombinant YFV provides for expression of the exogenous nucleic acid in the cell and production of the polypeptide encoded by the exogenous nucleic acid, and wherein an immune response to the polypeptide antigen is elicited.

16. The method of claim 15, wherein the antigen is a host antigen.

17. The method of claim 15, wherein the antigen is an antigen associated with a pathogenic microorganism other than the parent YFV.

18. A method of eliciting an immune response to a tumor-associated antigen in an individual, the method comprising administering a recombinant YFV of claim 1 to a mammalian subject, wherein the recombinant YFV comprises a tumor-associated antigen/epitope-encoding nucleic acid, such that the recombinant flavivirus enters a cell of the mammalian subject, the tumor-associated antigen is expressed on the host cell surface and/or presented in the context of an MHC molecule, and an immune response is elicited to the tumor-associated antigen.

19. A method of producing an exogenous polypeptide, the method comprising introducing a recombinant bicistronic YFV of claim 1 into an isolated susceptible host cell under conditions that favor production of the exogenous polypeptide by the host cell.

20. The method of claim 19, further comprising purifying the exogenous polypeptide.

21. The recombinant YFV of claim 1, wherein the polypeptide encoded by the exogenous nucleic acid has a length of from about 4 amino acids to about 1000 amino acids.

22. The recombinant YFV of claim 1, wherein the polypeptide encoded by the exogenous nucleic acid has a length of from about 10 amino acids to about 1000 amino acids.

23. The recombinant YFV of claim 1, wherein the polypeptide encoded by the exogenous nucleic acid has a length of from about 20 amino acids to about 1000 amino acids.

24. The recombinant YFV of claim 1, wherein the polypeptide encoded by the exogenous nucleic acid has a length of from about 30 amino acids to about 1000 amino acids.

* * * * *